United States Patent [19]

Cascieri et al.

[11] Patent Number: 5,621,079
[45] Date of Patent: Apr. 15, 1997

[54] NEUROPEPTIDE Y RECEPTOR

[75] Inventors: Margaret A. Cascieri, E. Windsor; David L. Linemeyer, Westfield; Douglas J. Macneil, Westfield; Lin-Lin Shiao, Avenel; Catherine D. Strader, Verona; David H. Weinberg, Westfield; Carina P. Tan, Metuchen, all of N.J.

[73] Assignee: Merck & Co., Inc., Rahway, N.J.

[21] Appl. No.: 415,818

[22] Filed: Apr. 3, 1995

Related U.S. Application Data

[63] Continuation-in-part of Ser. No. 383,746, Feb. 3, 1995.
[51] Int. Cl.$^6$ .................................................. C07K 14/705
[52] U.S. Cl. ............................................ 530/350; 435/69.1
[58] Field of Search .......................... 530/350; 435/69.1

[56] References Cited

FOREIGN PATENT DOCUMENTS

93/09227 5/1993 WIPO .
93/24515 12/1993 WIPO .

OTHER PUBLICATIONS

L. Grundemar and R. Hakanson, TiPS—May 1994 [vol. 15], entitled Neuropeptide Y effector systems: perspectives for drug development.

C.J. Billington & A.S. Levine, Neurobiology, 1992, 2:847–851, entitled Hypothalamic neuropeptide Y regulation of feeding and energy metabolism.

A.S. Levine & J.E. Morley, Peptides, 1984, 5:1025–1029, entitled Neuropeptide Y: A Potent Inducer of Consummatory Behavior in Rats.

Grundemar, L., et al., Characterization of vascular neuropeptide Y receptors Br. J. Pharmacol. 1992.105 (1):pp. 45–50.

Wahlestedt, C., et al., Evidence for different pre- and post-junctional receptors for neuropeptide Y and related peptides, Regul. Pept. 1986.13 (3–4):pp. 307–318.

Jorgensen et al., Structure–function studies on neuropeptide Y and pancreatic polypeptide—evidence for two PP-fold receptors in vas deferens, Eur. J. Pharmacol. 1990. 186 (1): pp. 105–114.

Cox, H.M., et al., The Effects of Selective Amino Acid Substitution Upon Neuropeptide Y Antisecretory Potency in Rat Jejunum Mucosa, Peptides, 1991. 12(2): pp. 323–327.

Wahlestedt, C., et al., Identification of Cultured Cells Selectively Expressing Y1–, Y2–, or Y3–Type Receptors for Neuropeptide Y/Peptide YY, Life Sciences, 1992. 50: pp. PL7–PL12.

Balasubrananian, A., et al., Characterization of Neuropeptide Y Binding Sites in Rat Cardiac Ventricular Membranes 1, Peptides 1990. 11(3):pp. 545–550.

Li, X.J., et al., Cloning, Functional Expression, and Developmental Regulation of a Neuropeptide Y Receptor from *Drosophila melangaster**, J. Biol. Chem., 1992. 267(1): pp. 9–12.

Jolicoeur, F.B., In Vivo Structure Activity Study Supports the Existence of Heterogeneous Neuropeptide Y Receptors, Brain Res. Bull., 1991. 26(2): pp. 309–311.

Liebowitz & Alexander, Analysis of Neuropeptide Y–Induced Feeding: Dissociation of Y1 and Y2 Receptor Effects on Natural Meal Patterns, Peptides, 1991. 12(6): pp. 1251–1260.

B.G. Stanley, et al., Peptides, 1992, 13:581–587, entitled Evidence for Neuropeptide Y Mediation of Eating Produced by Food Deprivation and for a Variant of the Y1 Receptor Mediating This Peptide's Effect.

H. Herzog, et al., Proc. Natl. Acad. Sci., 1992, 89:5794–5798, entitled Cloned human neuropeptide Y receptor couples to two different messenger system.

D. Larhammar, et al., J. Biol. Chem., 1992, 267(16):10935–10938, entitled Cloning and Functional Expression of a Human Neuropeptide Y/Peptide YY Receptor of the Y1 Type.

C. Eva, et al., FEBS, 1990, vol. 271, number 1, 2, 81–84, entitled Molecular cloning of a novel G protein–coupled receptor that may belong to the neuropeptide receptor family.

C. Wahlestedt & D.J. Reis, Annu. Rev. Pharmacol. Toxicol., 1993, 32:309–352, entitled Neuropeptide Y–Related Peptides and their Receptors—Are the Receptors Potential Therapeutic Drug Targets?.

Strader, C.D., I.S. Sigal, and R.A. Dixon, Structural basis of beta–adrenergic receptor function. FASEB–J, 1989. 3(7): pp. 1825–1832.

Dube, M. G., et al., Evidence that neuropeptide–Y is a physiological signal for normal food–intake, Brain Research, 1994, 646:341–344.

*Primary Examiner*—Stephen G. Walsh
*Assistant Examiner*—Stephen Gucker
*Attorney, Agent, or Firm*—Mary A. Appollina; Melvin Winokur

[57] ABSTRACT

A novel mammalian neuropeptide Y receptor and method of making the receptor are provided. The invention includes DNA encoding the receptor, the receptor, assays employing the receptor, cells expressing the receptor, antibodies which bind specifically to the receptor, RNA encoded by the DNA sequence or its complementary sequence, and single-stranded DNA with a sequence complementary to the RNA which encodes the receptor. The receptor and assays employing the receptor are useful for identifying compounds which bind to the receptor, including specific modulators of the receptor. Such compounds are useful for treating a variety of disease conditions, including obesity, diabetes, anxiety, hypertension, cocaine withdrawal, congestive heart failure, memory enhancement, cardiac and cerebral vasospasm, pheochromocytoma and ganglioneuroblastoma, and Huntington's, Alzheimer's and Parkinson's diseases.

8 Claims, 12 Drawing Sheets

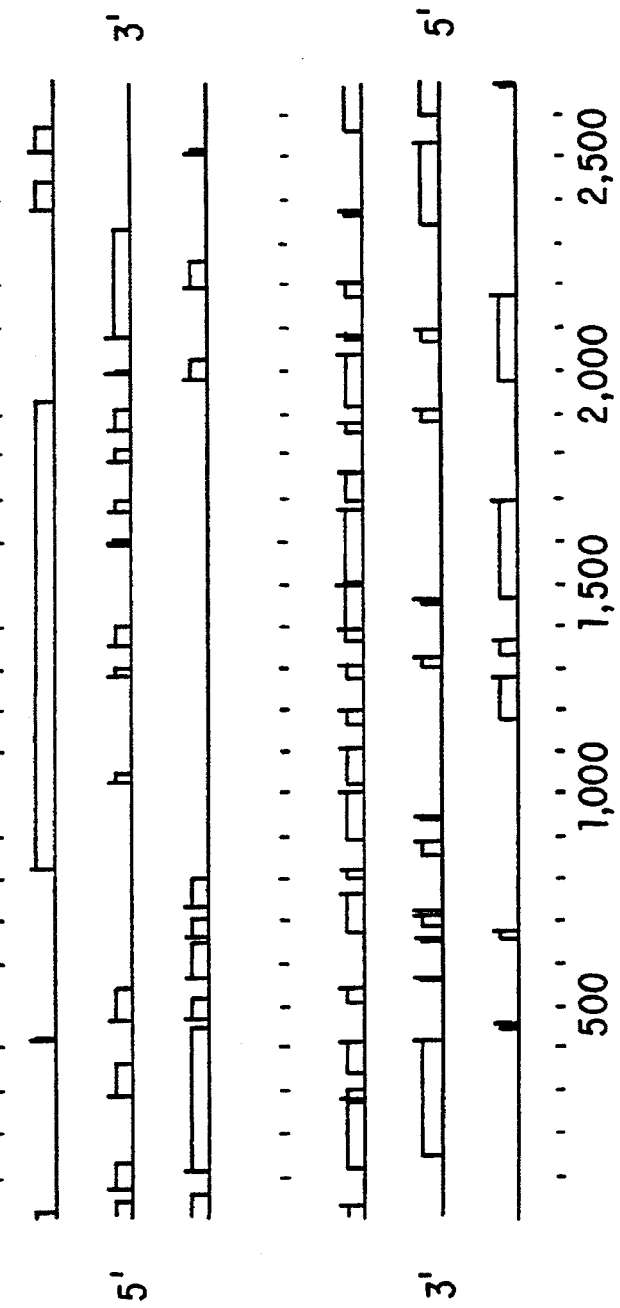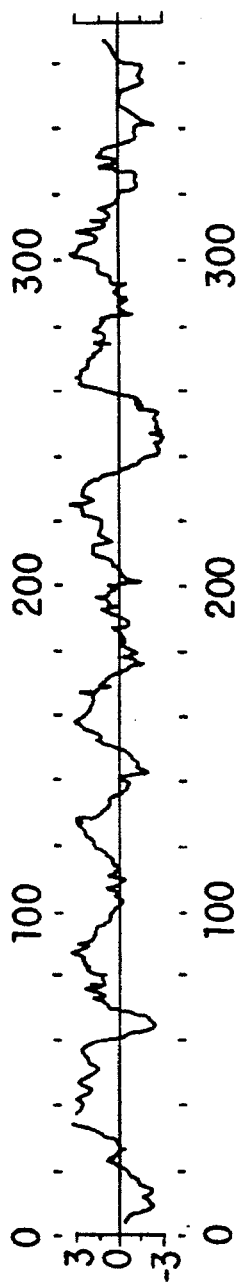

```
          10                  30                  50
           .                   .                   .
CTGCAGTCTATTGGATGAAGAGTGTACATATTCATATAATTCTTAAAGTA 70                  90
                     .                   .
     GGCAGAAATTAAAGGGGATGGAAATATATACTTGTACTGCCTTAGATAGT 110                 130                 150
           .                   .                   .
     CACCAGGATGTTGTTACAGTCTTCGTTTACTGCTTCTGAAGCCTATACTG 170                 190
                     .                   .
     ATAGAATTAATAAAATACTGAGAGAGAGAGAGAGGGACAGAGAGAGAGAG 210                 230                 250
           .                   .                   .
     GGGGAGAGAGAGAGAGAGAGAGAGAGAGAGAGAGAGAGAGAGAGAGAGAG 270                 290
                     .                   .
     AGAAGAGAAGAAAACAAGGTAAGCCATCTGCTTAACTTATGTCCACATTC 310                 330                 350
           .                   .                   .
     TCTCAAGAGCATTGTCCTATTTGTAGAATTATCTATATTGTTAAGAATCA 370                 390
                     .                   .
     TCTCCATTGTTAAGATTTTGTGGGCTGGAGATCCAGCTCTGTTGATAAAG 410                 430                 450
           .                   .                   .
     TGCTTGCCTAACATGCATGAAGTCCTAGGTTCTATTCCCAAGGCTACATA 470                 490
                     .                   .
     AAACCTTGTGTTGTGATGAATGCCTGTAATCCCAGTACGCAGCAAGGAGA
```

FIG.3A

```
          510              530              550
           .                .                .
GACAAGGAGGATCAGAAGCTTAAGGACATCATTTTGTACATAGTGAGTTT 570              590
                    .                .
         GAGGAAAGCTGAGGTTACATGGAACTCTCTCTCTCAAAAACAAAACAA 610              630              650
           .                .                .
AACAAAACAAAACCTTCTACTAATATTCTGGATTCTGTTTGATTTTTAGG 670              690
                    .                .
         ATCTCAAGAGCATGCTGACGTCATTTATGTGTTTCCATCAGATACAGACA 710              730              750
           .                .                .
GAGATCATAAACATTTAACTCATTGATTATATGTTGAGAGTTGTCCCTCA 770              790
                    .                .
         AGAACCAATGGCCAAACATCCACTGAGGATACACGGAAGCTTAGAAAATC 810              830              850
           .                .                .
TCTAATTAAAATCCTGACATAATGGAAGTGCTCACAAACCAGCCAACACC
                                MetGluValLeuThrAsnGlnProThrPr 870              890
                    .                .
         TAATAAAACCAGTGGCAAGAGCAACAACTCGGCATTTTTCTACTTTGAAT
         oAsnLysThrSerGlyLysSerAsnAsnSerAlaPhePheTyrPheGluS 910              930              950
           .                .                .
CCTGCCAACCCCCTTTTCTAGCCATACTCTTGCTACTCATAGCATATACT
erCysGlnProProPheLeuAlaIleLeuLeuLeuLeuIleAlaTyrThr
```

FIG. 3B

```
          970              990
GTGATCCTAATCATGGGCATTTTTGGAAACCTCTCTCTTATCATCATCAT
ValIleLeuIleMetGlyIlePheGlyAsnLeuSerLeuIleIleIl 1010           1030           1050
CTTTAAGAAACAGAGAGAAGCTCAAAATGTTACCAACATACTGATTGCCA
ePheLysLysGlnArgGluAlaGlnAsnValThrAsnIleLeuIleAlaA 1070             1090
ACCTGTCCCTCTCTGACATCTTGGTGTGTGTCATGTGCATCCCTTTTACG
snLeuSerLeuSerAspIleLeuValCysValMetCysIleProPheThr 1110           1130           1150
GTCATCTACACTCTGATGGACCACTGGGTATTTGGGAACACTATGTGTAA
ValIleTyrThrLeuMetAspHisTrpValPheGlyAsnThrMetCysLy 1170             1190
ACTCACTTCCTACGTGCAAAGTGTCTCAGTTTCTGTGTCCATATTCTCCC
sLeuThrSerTyrValGlnSerValSerValSerValSerIlePheSerL 1210           1230           1250
TTGTGTTGATTGCTATTGAACGATATCAGCTGATTGTGAACCCCCGTGGC
euValLeuIleAlaIleGluArgTyrGlnLeuIleValAsnProArgGly 1270             1290
TGGAAACCCAGAGTAGCTCATGCCTATTGGGGGATCATCTTGATTTGGCT
TrpLysProArgValAlaHisAlaTyrTrpGlyIleIleLeuIleTrpLe 1310           1330           1350
CATTTCTCTGACATTGTCTATTCCCTTATTCCTGTCCTACCACCTCACCA
uIleSerLeuThrLeuSerIleProLeuPheLeuSerTyrHisLeuThrA
```

FIG. 3C

```
              1370              1390
               .                 .
ATGAGCCCTTTCATAATCTCTCTCCCTACTGACATCTACACCCACCAG
snGluProPheHisAsnLeuSerLeuProThrAspIleTyrThrHisGln 1410             1430              1450
         .                .                 .
GTAGCTTGTGTGGAGATTTGGCCTTCTAAACTGAACCAACTCCTCTTTTC
ValAlaCysValGluIleTrpProSerLysLeuAsnGlnLeuLeuPheSe 1470              1490
               .                 .
TACATCATTATTTATGCTCCAGTATTTTGTCCCTCTGGGTTTCATTCTTA
rThrSerLeuPheMetLeuGlnTyrPheValProLeuGlyPheIleLeuI 1510             1530              1550
         .                .                 . .
TCTGCTACCTGAAGATCGTTCTCTGCCTCCGAAAAAGAACTAGGCAGGTG
leCysTyrLeuLysIleValLeuCysLeuArgLysArgThrArgGlnVal 1570              1590
               .                 .
GACAGGAGAAAGGAAAATAAGAGCCGTCTCAATGAGAACAAGAGGGTAAA
AspArgArgLysGluAsnLysSerArgLeuAsnGluAsnLysArgValAs 1610             1630              1650
         .                .                 .
TGTGATGTTGATTTCCATCGTAGTGACTTTTGGAGCCTGCTGGTTGCCCT
nValMetLeuIleSerIleValValThrPheGlyAlaCysTrpLeuProL 1670              1690
               .                 .
TGAACATTTTCAATGTCATCTTCGACTGGTATCATGAGATGCTGATGAGC
euAsnIlePheAsnValIlePheAspTrpTyrHisGluMetLeuMetSer 1710             1730              1750
         .                .                 .
TGCCACCACGACCTGGTATTTGTAGTTTGCCACTTGATTGCTATGGTTTC
CysHisHisAspLeuValPheValValCysHisLeuIleAlaMetValSe
```

FIG. 3D

```
                    1770                      1790
                     .                         .
      TACTTGCATAAATCCTCTCTTTTATGGATTTCTCAACAAAAACTTCCAGA
      rThrCysIleAsnProLeuPheTyrGlyPheLeuAsnLysAsnPheGlnL 1810                  1830                  1850
           .                    .                      .
      AGGATCTAATGATGCTTATTCACCACTGTTGGTGTGGTGAACCTCAGGAA
      ysAspLeuMetMetLeuIleHisHisCysTrpCysGlyGluProGlnGlu 1870                      1890
                     .                         .
      AGTTATGAAAATATTGCCATGTCTACTATGCACACAGATGAATCCAAGGG
      SerTyrGluAsnIleAlaMetSerThrMetHisThrAspGluSerLysGl 1910                  1930                  1950
           .                    .                      .
      ATCATTAAAACTGGCTCACATACCAACAGGCATATAGAAACTGGTAAGCA
      ySerLeuLysLeuAlaHisIleProThrGlyIleEnd 1970                      1990
                     .                         .
      AAATCAAAGCCCTTCTGTTATGAAAGAAAGAGAAGAAATAGTATGGAATA 2010                  2030                  2050
           .                    .                      .
      GGGCAAGGTGCAGAGGAAGCCAGACTTAAACACATAATATCTTTGGGCCC 2070                      2090
                     .                         .
      AGTTTTGCTTTAAGTTAAGCATGTCTACTCCATTCAGCCATAGAACACAC 2110                  2130                  2150
           .                    .                      .
      AGAGATTTATCCCTACCCTTTCTTTTTTTCCTTTGGAAGAATAATAACTT 2170                      2190
                     .                         .
      AAACAACCTAGACATCATTACTGAGGAAGAGAACAAAAATGAGAGAGCAT
```

FIG. 3E

```
            2210                  2230                   2250
ACAAGGACAGCAGAGATGTCTGGGGTACAAAATTCACGTTATTCGCTGGA

2270

ATAGCTAGAAAGTTATTAGTTGTGCTGCAG
```

1   MEVLTNQPTPNKTSGKSNNSAFFYFES..CQPPFLAILLLLIAYTVIL  46
        .:::.. ....    .|:||:::  ||.   |:  |:  .|:  |  :||..::
  1   MNSTLFSKVENHSIHYNASENSPLLAFENDDCHLPLAVIFTLALAYGAVI  50

-TM1----------|                |----------TM2-------

47   IMGIFGNLSLIIIIFKKQREAQNVTNILIANLSLSDILVCVMCIPFTVIY  96
      |:|: |||.||||||: ||:| .|||||||.|||:||:||.|||:|||.:|
 51   ILGVSGNLALIIIIL.KQKEMRNVTNILIVNLSFSDLLVAVMCLPFTFVY  99

--|           |----------TM3--------|

97   TLMDHWVFGNTMCKLTSYVQSVSVSVSIFSLVLIAIERYQLIVNPRGWKP  146
      |||||||||:|||||..:||:||:.|||||||||||:||.|||:||||||:|
100   TLMDHWVFGETMCKLNPFVQCVSITVSIFSLVLIAVERHQLIINPRGWRP  149

|----------TM4-----------|     *

147   RVAHAYWGIILIWLISLTLSIPLFLSYHLTNEPFHNLSLPTDIYTHQVAC  196
      .  ||| ||.:||::::. |:|:.:    ||:|||:|:||:.  :.... .|
150   NNRHAYIGITVIWVLAVASSLPFVIYQILTDEPFQNVSLAA..FKDKYVC  197

|----------TM5----------|

197   VEIWPSKLNQLLFSTSLFMLQYFVPLGFILICYLKIVLCLRKRTRQVDRR  246
      .: :||. :.| :.| |::||||.||.||:|||:||  : |::|.. :|:
198   FDKFPSDSHRLSYTTLLLVLQYFGPLCFIFICYFKIYIRLKRRNNMMDKI  247

|-----------TM6-----------|

KENKSRLNENKRVNVMLISIVVTFGACWLPLNIFNVIFDWYHEMLMSCHH  296
      :::| |  .|.||:|:||:||||.|:-|||||.|||.:|||  |::::.|:|
248   RDSKYRSSETKRINIMLLSIVVAFAVCWLPLTIFNTVFDWNHQIIATCNH  297

|----------TM7----------|

297   DLVFVVCHLIAMVSTCINPLFYGFLNKNFQKDLMMLIHHCWCGEPQESYE  346
      :|:|:::|||.||:|||:||:||||||||||||:||  ::::  |   ..:::||
298   NLLFLLCHLTAMISTCVNPIFYGFLNKNFQRDLQFFFNFCDFRSRDDDYE  347
```

FIG. 4A

```
347 NIAMSTMHTDESKGSLKLAHIPTGI*........... 372
    .||||||||| ||.||| |   |.::
348 TIAMSTMHTDVSKTSLKQA.SPVAFKKISMNDNEKV* 383
```

FIG. 4B

```
  1 CCCCGGGCTG CAGGAATTCC CACATGTTTC CATCAAATAC AGACACAGAT
 51 CAGGGAAGAT TAAACCCTAC TAATTTCTCG TCGGATGCCT CACAACAAGG
101 TGCCTTCCAA GAACTAATGG CCAAAATATC CACCCACAAC ACAAATAAGC
151 TTAGAAAATC TCTTCTTACA ATCCTGACAC AATGGAAGTT TCCCTAAACC
201 ACCCAGCATC TAATACAACC AGCACAAAGA ACAACAACTC GGCATTTTTT
251 TACTTTGAGT CCTGTCAACC CCCTTCTCCA GCTTTACTCC TATTATGCAT
301 AGCCTATACT GTGGTCTTAA TTGTGGGCCT TTTTGGAAAC CTCTCTCTCA
351 TCATCATCAT CTTTAAGAAG CAGAGAAAAG CTCAGAATTT CACCAGCATA
401 CTGATTGCCA ATCTCTCCCT CTCTGATACC TTGGTGTGTG TCATGTGCAT
451 CCATTTTACT ATCATCTACA CTCTGATGGA CCACTGGATA TTTGGGGATA
501 CCATGTGCAG ACTCACATCC TATGTGCAGA GTGTCTCAAT CTCTGTGTCC
551 ATATTCTCAC TTGTATTCAC TGCTGTCGAA AGATATCAGC TAATTGTGAA
601 CCCCCGTGGC TGGAAGCCCA GTGTGACTCA TGCCTACTGG GGCATCACAC
651 TGATTTGGCT GTTTTCCCTT CTGCTGTCTA TTCCCTTCTT CCTGTCCTAC
701 CACCTCACTG ATGAGCCCTT CCACAACCTC TCTCTCCCCA CTGACCTCTA
751 CACCCACCAG GTGGCCTGTG TGGAGAACTG GCCCTCCAAA AAGGACCGGC
801 TGCTCTTCAC CACCTCCCTT TTTCTGCTGC AGTATTTTGT TCCTCTAGGC
851 TTCATCCTCA TCTGCTACTT GAAGATTGTT ATCTGCCTCC GCAGGAGAAA
901 TGCAAAGGTA GATAAGAAGA AGGAAAATGA GGGCCGGCTC AATGAGAACA
951 AGAGGATCAA CACAATGTTG ATTTCCATCG TGGTGACCTT TGGAGCCTGC
```

FIG. 5A

```
1001 TGGCTGCCCC CGAATATCTT CAATGTCATC TTTGACTGGT ATCATGAGGT

1051 GCTGATGAGC TGCCACCACG ACCTGGTATT TGTAGTTTGC CACTTGGTTG

1101 CTATGGTTTC CACATGTATA AACCCTCTCT TTTATGGCTT TCTCAACAAA

1151 AATTTCCAAA AGGACCTGGT AGTGCTTATT CACCACTGCT GGTGCTTCAC

1201 ACCTCAGGAA AGATGTGAAA ATATTGCCAT CTCCACTATG CACACAGACT

1251 CCAAGAGGTC TTTAAGATTG GCTCGTATAA CAACAGGTAT ATGAAAATTG

1301 ATAATGCTGA AGCTCTTCTT GAATGGGAGC TGGACAGGTA ATGGTGGGAA

1351 TAGGGCAAGA TGCAGAAAGA AGAAACCAGA ACCAAAAATA GCAACTTTAT

1401 ACCCACTTTT CCTTTAGGCT AAGACTGCCT GTCTCATATG TCTATCCAAC

1451 ACACCCTCCG GAATTCGATA TCAAGCTTAT CGATACCGTC GACCTCGAG
```

FIG. 5B

```
  1  MEVSLNHPAS NTTSTKNNNS AFFYFESCQP PSPALLLLCI AYTVVLIVGL

51  FGNLSLIIII FKKQRKAQNF TSILIANLSL SDTLVCVMCI HFTIIYTLMD

101  HWIFGDTMCR LTSYVQSVSI SVSIFSLVFT AVERYQLIVN PRGWKPSVTH

151  AYWGITLIWL FSLLLSIPFF LSYHLTDEPF HNLSLPTDLY THQVACVENW

201  PSKKDRLLFT TSLFLLQYFV PLGFILICYL KIVICLRRRN AKVDKKKENE

251  GRLNENKRIN TMLISIVVTF GACWLPPNIF NVIFDWYHEV LMSCHHDLVF

301  VVCHLVAMVS TCINPLFYGF LNKNFQKDLV VLIHHCWCFT PQERCENIAI

351  STMHTDSKRS LRLARITTGI
```

FIG. 6

NEUROPEPTIDE Y RECEPTOR

BACKGROUND OF THE INVENTION

This application is a continuation-in-pan of copending application Ser. No. 08/383,746, filed Feb. 3, 1995, the contents of which are hereby incorporated by reference.

Neuropeptide Y (NPY) is a 36 residue, amidated polypeptide. It is anatomically co-distributed and co-released with norepinephrine in and from sympathetic postganglionic neurons ([1], [2], [3], [4], [5], [6]). Stimulation of the sympathetic nervous system under physiological circumstances such as exercise ([7], [8]) or exposure to the cold ([9], [10]) promotes an elevation of both norepinephrine and NPY.

NPY is believed to act in the regulation of appetite control ([11], [12]) and vascular smooth muscle tone ([13], [14]) as well as regulation of blood pressure ([6], [15], [16], [17]). NPY also decreases cardiac contractility ([18], [19], [20], [21], [22]). Congestive heart failure and cardiogenic shock are associated with probable releases of NPY into the blood ([23], [24], [25]). Regulation of NPY levels may be beneficial to these disease states [26].

At the cellular level, neuropeptide Y binds to a G-protein coupled receptor ([27], [28], [29], [30]). Neuropeptide Y is involved in regulating eating behavior and is an extremely potent orixigenic agent ([11], [12], [31]). When administered intracerebroventricularly or injected into the hypothalamic paraventricular nucleus (PVN) it elicits eating in satiated rats ([32], [33], [34]) and intraventricular injection of antisera to NPY decreases eating ([11], [31]). It has been shown to stimulate appetite in a variety of species and at different stages of development ([12]). Other effects on energy metabolism include decreased thermogenesis, body temperature and uncoupling protein, and increased white fat storage and lipoprotein lipase activity ([9], [35], [36], [37], [38], [39]). NPY levels in the PVN increase upon fasting ([40], [41], [42], [43], [44]), before a scheduled meal ([31], [36], [40]), and in both streptozotocin-induced and spontaneous diabetes ([36], [45], [46], [47], [48], [49]). Also, NPY levels are increased in genetically obese and hyperphagic Zucker rats ([36], [50], [51]). Thus, a specific centrally acting antagonist for the appropriate NPY receptor subtype may be therapeutically useful for treating obesity and diabetes. Other disorders which might be targeted therapeutically include anxiety, hypertension, cocaine withdrawal, congestive heart failure, memory enhancement, cardiac and cerebral vasospasm, pheochromocytoma and ganglioneuroblastoma, and Huntington's, Alzheimer's and Parkinson's diseases ([26], [52]).

At least four receptor subtypes of the NPY family have been proposed based on pharmacological and physiological properties. The Y1 receptor is stimulated by NPY or PYY (peptide YY) and appears to be the major vascular receptor ([16], [53], [54], [55]). The Y2 receptor is stimulated by C-terminal fragments of NPY or PYY and is abundantly expressed both centrally and peripherally ([55], [56], [57], [58]). A third receptor (Y3) is exclusively responsive to NPY and is likely present in adrenal medulla, heart, and brain stem ([27], [59]). In addition, other subtypes of this receptor family are known to exist, based on pharmacological and physiological characterization ([60], [61], [62], [63]). The feeding behavior is stimulated potently by NPY, $NPY_{2-36}$ and the Y 1 agonist [Leu31, Pro34]NPY, but is not stimulated by the Y2 agonist $NPY_{13-36}$ ([11], [64], [65], [66]). This pharmacology is not characteristic of the defined Y 1, Y2 or Y3 receptors and can thus be attributed to a unique receptor, termed "atypical Y1" ([11], [65], [66]), that is responsible for evoking the feeding response. In addition, data indicate the existence of additional members of this receptor family including one subtype specific for peptide PP ([62], [63]), one with affinity for short C-terminal fragments of NPY which induce hypotension when administered systemically ([15], [17], [30], [67], [68]), and one associated with binding of NPY and PYY to brain sigma and phencyclidine binding sites ([61]).

The Y1 receptor has been cloned and shown to be a G-protein coupled receptor ([53], [69], [70]). Until the invention described herein of a novel NPY receptor, other NPY receptors had not been cloned.

References

1. DeQuidt, M. E. and P. C. Emson, *Distribution of neuropeptide Y-like immunoreactivity in the rat central nervous system—II. Immunohistochemical analysis.* Neuroscience, 1986. 18(3): p. 545–618.
2. Lundberg, J. M., et al., *Co-release of neuropeptide Y and catecholamines during physical exercise in man.* Biochem Biophys Res Commun, 1985. 133(1): p. 30–6.
3. Morris, M. J., et al., *Increases in plasma neuropeptide Y concentrations during sympathetic: activation in man.* J Auton Nerv Syst, 1986. 17(2): p. 143–9.
4. Pernow, J., *Co-release and functional interactions of neuropeptide Y and noradrenaline in peripheral sympathetic vascular control.* Acta Physiol Scand Suppl, 1988. 568(1 ): p. 1–56.
5. Sawchenko, P. E., et al., *Colocalization of neuropeptide Y immunoreactivity in brainstem catecholaminergic neurons that project to the paraventricular nucleus of the hypothalamus.* J Comp Neurol, 1985.241(2): p. 138–53.
6. Wahlestedt, C., et al., *Norepinephrine and neuropeptide Y: vasoconstrictor cooperation in vivo and in vitro.* Am J Physiol, 1990. 258: p. R736–R742.
7. Kaijser, L., et al., *Neuropeptide Y is released together with noradrenaline from the human heart during exercise and hypoxia.* Clin Physiol, 1990. 10(2): p. 179–88.
8. Lewis, D. E., et at., *Intense exercise and food restriction cause similar hypothalamic neuropeptide Y increases in rats.* Am J Physiol, 1993. 264: p. E279–E284.
9. McCarthy, H. D., et al., *Widespread increases in regional hypothalamic Neuropeptide-Y levels in acute Cold-Exposed rats.* Neuroscience, 1993. 54(1): p. 127–132.
10. Zukowska, G. Z. and A. C. Vaz, *Role of neuropeptide Y (NPY) in cardiovascular responses to stress.* Synapse, 1988. 2(3): p. 293–8.
11. Stanley, B. G., et al., *Evidence for neuropeptide Y mediation of eating produced by food deprivation and for a variant of the Y1 receptor mediating this peptide's effect.* Peptides, 1992. 13: p. 581–587.
12. Stanley, B. G., *Neuropeptide Y in multiple hypothalamic sites controls eating behavior, endocrine, and autonomic systems for body energy balance,* in *Neuropeptide Y,* W. F. Colmers and C. Wahlestedt, Editor. 1993, Humana Press: Totowa, N.J. p. 457–509.
13. Abel, P. W. and C. Han, *Effects of neuropeptide Y on contraction, relaxation, and membrane potential of rabbit cerebral arteries.* J Cardiovasc Pharmacol, 1989. 13( 1 ): p. 52–63.

14. Han, C. and P. W. Abel, *Neuropeptide Y potentiates contraction and inhibits relaxation of rabbit coronary arteries.* J Cardiovasc Pharmacol, 1987. 9(6): p. 675–81.

15. Grundemar, L., et al., *Biphasic blood pressure response to neuropeptide Y in anesthetized rats.* Eur J Pharmacol, 1990. 179(1–2): p. 83–7.

16. Grundemar, L., et al., *Characterization of vascular neuropeptide Y receptors.* Br J Pharmacol, 1992. 105(1): p. 45–50.

17. Shen, S. H., et al., *C-terminal neuropeptide Y fragments are mast cell-dependent vasodepressor agents.* Eur. J. Pharmacol., 1993. 204: p. 249–256.

18. Tseng, C. J., et al., *Cardiovascular effects of neuropeptide Y in rat brainstem nuclei.* Circ Res, 1989. 64(1): p. 55–61.

19. Carter, D. A., M. Vallejo, and S. L. Lightman, *Cardiovascular effects of neuropeptide Y in the nucleus tractus solitarius of rats: relationship with noradrenaline and vasopressin.* Peptides, 1985. 6(3): p. 421–5.

20. Grundemar, L., C. Wahlestedt, and D. J. Reis, *Neuropeptide Y acts at an atypical receptor to evoke cardiovascular depression and to inhibit glutamate responsiveness in the brainstem.* J Pharmacol Exp Ther, 1991. 258(2): p. 633–8.

21. Grundemar, L., C. Wahlestedt, and D. J. Reis, *Long-lasting inhibition of the cardiovascular responses to glutamate and the baroreceptor reflex elicited by neuropeptide Y injected into the nucleus tractus solitarius of the rat.* Neurosci Lett, 1991. 122(1): p. 135–9.

22. Zukowska-Grojec, Z. and C. Wahlestedt, *Origin and actions of neuropeptide Y in the cardiovascular system,* in *Neuropeptide Y,* W. F. Colmers and C. Wahlestedt, Editor. 1993, Humana Press: Totowa, N.J. p. 315–388.

23. Edvinsson, L., et al., *Congestive heart failure: involvement of perivascular peptides reflecting activity in sympathetic, parasympathetic and afferent fibres.* Eur J Clin Invest, 1990. 20(1): p. 85–9.

24. Franco, C. A., et al., *Release of neuropeptide Y and noradrenaline from the human heart after aortic occlusion during coronary artery surgery.* Cardiovasc Res, 1990. 24(3): p. 242–6.

25. Maisel, A. S., et al., *Elevation of plasma neuropeptide Y levels in congestive heart failure.* Am J Med, 1989. 86(1): p. 43–8.

26. Wahlestedt, C. and D. J. Reis, *Neuropeptide Y-related peptides and their receptors—are the receptors potential therapeutic drug targets?* Annu. Rev. Pharmacol. Toxicol., 1993.32: p. 309–352.

27. Wahlestedt, C., S. Regunathan, and D. J. Reis, *Identification of cultured cells selectively expressing Y1-, Y2-, or Y3-type receptors for neuropeptide Y/peptide YY.* Life Sciences, 1992. 50: p. PL7–PL12.

28. Feth, F., W. Rascher, and M. C. Michel, *G-protein coupling and signalling of Y1-like neuropeptide Y receptors in SK-N-MC cells.* Naunyn Schmiedebergs Arch Pharmacol, 1991. 344(1): p. 1–7.

29. Motulsky, H. J. and M. C. Michel, *Neuropeptide Y mobilizes $Ca^{2+}$ and inhibits adenylate cyclase in human erythroleukemia cells.* Am J Physiol, 1988. 255: p. E880–E885.

30. Wahlestedt, C., et al., *Neuropeptide Y receptor subtypes, Y1 and Y2.* Ann N Y Acad Sci, 1990. 611 (7): p. 7–26.

31. Sahu, A. and S. P. Kalra, *Neuropeptidergic regulation of feeding-behavior—neuropeptide-Y.* Trends In Endocrinology And Metabolism, 1993. 4(7): p. 217–224.

32. Clark, J. T., et al., *Neuropeptide Y and human pancreatic polypeptide stimulate feeding behavior in rats.* Endocrinology, 1984. 115(1): p. 427–429.

33. Stanley, B. G. and S. F. Leibowitz, *Neuropeptide Y injected in the paraventricular hypothalamus: a powerful stimulant of feeding behavior.* Proc. Natl. Acad. Sci. USA, 1985. 82: p. 3940–3943.

34. Stanley, B. G. and S. F. Leibowitz, *Neuropeptide Y: stimulation of feeding and drinking by injection into the paraventricular nucleus.* Life Sci, 1984. 35(26): p. 2635–42.

35. Zarjevski, N., et al., *Chronic intracerebroventricular neuropeptide-Y administration to normal rats mimics hormonal and metabolic changes of obesity.* Endocrinology, 1993. 133(4): p. 1753–1758.

36. Billington, C. J. and A. S. Levine, *Hypothalamic neuropeptide Y regulation of feeding and energy metabolism.* Current Opinion in Neurobiology, 1992. 2: p. 847–851.

37. Leibowitz, S. F., *Brain neuropeptide Y: an integrator of endocrine, metabolic and behavioral processes.* Brain Research Bulletin, 1991. 27: p. 333–337.

38. Billington, C. J., et al., *Effects of intracerebroventricular injection of neuropeptide Y on energy metabolism.* Am. J. Physiol., 1991. 260: p. R321–R327.

39. Billington, C. J., et al., *Neuropeptide-Y in hypothalamic paraventricular nucleus—a center coordinating energy-metabolism.* American Journal Of Physiology, 1994. 266(6): p. R1765–R1770.

40. Kalra, S. P., et al., *Neuropeptide Y secretion increases in the paraventricular nucleus in association with increased appetite for food.* Proc. Natl. Acad. Sci. USA, 1991. 88: p. 10931–10935.

41. Beck, B., et al., *Rapid and localized alterations of neuropeptide Y in discrete hypothalamic nuclei with feeding status.* Brain Res, 1990. 528(2): p. 245–9.

42. Brady, L. S., et al., *Altered expression of hypothalamic neuropeptide mRNAs in food-restricted and food-deprived rats.* Neuroendocrinology, 1990. 52(5): p. 441–7.

43. Calza, L., et al., *Increase of neuropeptide Y-like immunoreactivity in the paraventricular nucleus of fasting rats.* Neurosci Lett, 1989. 104(1–2): p. 99–104.

44. Sahu, A., P. S. Kalra, and S. P. Kalra, *Food deprivation and ingestion induce reciprocal changes in neuropeptide Y concentrations in the paraventricular nucleus.* Peptides, 1988. 9(1): p. 83–6.

45. Abe, M., et al., *Increased neuropeptide Y content in the arcuatoparaventricular hypothalamic neuronal system in both insulin-dependent and non-insulin-dependent diabetic rats.* Brain Res, 1991. 539(2): p. 223–7.

46. Sahu, A., et al., *Neuropeptide-Y concentration in microdissected hypothalamic regions and in vitro release from the medial basal hypothalamus-preoptic area of streptozotocin-diabetic rats with and without insulin substitution therapy.* Endocrinology, 1990. 126(1): p. 192–8.

47. White, J. D., et al., *Increased hypothalamic content of preproneuropeptide-Y messenger ribonucleic acid in streptozotocin-diabetic rats.* Endocrinology, 1990. 126(2): p. 765–72.

48. Williams, G., et al., *Increased hypothalamic neuropeptide Y concentrations in diabetic rat.* Diabetes, 1988. 37(6): p. 763–72.

49. Williams, G., et al., *Increased neuropeptide Y concentrations in specific hypothalamic regions of streptozocin-induced diabetic rats.* Diabetes, 1989. 38(3): p. 321–7.

50. Beck, B., et al., *Hypothalamic neuropeptide Y (NPY) in obese Zucker rats: implications in feeding and sexual behaviors.* Physiol Behav, 1990. 47(3): p. 449–53.

51. Sanacora, G., et al., *Increased hypothalamic content of preproneuropeptide Y messenger ribonucleic acid in genetically obese Zucker rats and its regulation by food deprivation.* Endocrinology, 1990. 127(2): p. 730–7.

52. Wahlestedt, C., R. Ekman, and E. Widerlov, *Neuropeptide Y (NPY) and the central nervous system: distribution effects and possible relationship to neurological and psychiatric disorders.* Prog Neuropsychopharmacol Biol Psychiatry, 1989. 13(1–2): p. 31–54.

53. Larhammar, D., et al., *Cloning and functional expression of a human neuropeptide Y/peptide YY receptor of the Y1-type.* J. Biol. Chem., 1992. 267: p. 10935–10938.

54. Sheikh, S. P., et al., *Localization of Y1 receptors for NPY and PYY on vascular smooth muscle cells in rat pancreas.* Am J Physiol, 1991. 260: p. G250–G257.

55. Wahlestedt, C., N. Yanaihara, and R. Hakanson, *Evidence for different pre-and post-junctional receptors for neuropeptide Y and related peptides.* Regul Pept, 1986. 13(3–4): p. 307–18.

56. Jorgensen, J. C., J. Fuhlendorff, and T. W. Schwartz, *Structure-function studies on neuropeptide Y and pancreatic polypeptide—evidence for two PP-fold receptors in vas deferens.* Eur J Pharmacol, 1990. 186(1): p. 105–14.

57. Cox, H. M. and J. L. Krstenansky, *The effects of selective amino acid substitution upon neuropeptide Y antisecretory potency in rat jejunum mucosa.* Peptides, 1991. 12(2): p. 323–7.

58. Aicher, S. A., et al., *Receptor-selective analogs demonstrate NPY/PYY receptor heterogeneity in rat brain.* Neurosci Lett, 1991. 130(1): p. 32–6.

59. Balasubramaniam, A., et al., *Characterization of neuropeptide Y binding sites in rat cardiac ventricular membranes.* Peptides, 1990. 11(3): p. 545–50.

60. Li, X. J., et al., *Cloning, functional expression, and developmental regulation of a neuropeptide Y receptor from Drosophila melanogaster.* J Biol Chem, 1992. 267(1): p. 9–12.

61. Roman, F. J., et al., *Neuropeptide Y and peptide YY interact with rat brain sigma and PCP binding sites.* Eur J Pharmacol, 1989. 174(2–3): p. 301–2.

62. Schwartz, T. W., S. P. Sheikh, and M. M. O'Hare, *Receptors on phaeochromocytoma cells for two members of the PP-fold family-NPY and PP.* Febs Lett, 1987. 225(1–2): p. 209–14.

63. Schwartz, T. W., et al., *Signal epitopes in the three-dimensional structure of neuropeptide Y. Interaction with Y1, Y2, and pancreatic polypeptide receptors.* Ann N Y Acad Sci, 1990. 611(35): p. 35–47.

64. Wahlestedt, C., et al., *Modulation of anxiety and neuropeptide YY1 receptors by antisense oligodeoxynucleotides.* Science, 1993. 259: p. 528–531.

65. Jolicoeur, F. B., et al., *In vivo structure activity study supports the existence of heterogeneous neuropeptide Y receptors.* Brain Res Bull, 1991. 26(2): p. 309–11.

66. Leibowitz, S. F. and J. T. Alexander, *Analysis of neuropeptide Y-induced feeding: dissociation of Y1 and Y2 receptor effects on natural meal patterns.* Peptides, 1991. 12(6): p. 1251–60.

67. Inui, A., et al., *Characterization of peptide YY receptors in the brain.* Endocrinology, 1989. 124(1): p. 402–9.

68. Boublik, J., et al., *Neuropeptide Y and neuropeptide Y18–36. Structural and biological characterization.* Int J Pept Protein Res, 1989. 33(1): p. 11–5.

69. Eva, C., et al., *Molecular cloning of a novel G protein-coupled receptor that may belong to the neuropeptide receptor family.* FEBS Lett., 1990. 271: p. 81–84.

70. Herzog, H., et al., *Cloned human neuropeptide Y receptor couples to two different second messenger systems.* Proc Natl Acad Sci U.S.A., 1992. 89: p. 5794–5798.

SUMMARY OF THE INVENTION

The present invention relates to an isolated DNA sequence encoding a novel neuropeptide Y receptor, hereinafter referred to as the neuropeptide Y Yx receptor. The DNA sequence encoding the NPY Yx receptor has a sequence selected from a sequence as shown in FIG. 3, a sequence of substantial homology to the sequence shown in FIG. 3, a fragment of the sequence shown in FIG. 3, a fragment of the sequence of substantial homology to the sequence shown in FIG. 3, a sequence as shown in FIG. 5, a sequence of substantial homology to the sequence shown in FIG. 5, a fragment of the sequence shown in FIG. 5 or a fragment of the sequence of substantial homology to the sequence shown in FIG. 5.

In one embodiment of the invention is the isolated DNA sequence wherein the sequence is selected from a sequence as shown in FIG. 3, a sequence of substantial homology to the sequence shown in FIG. 3, a fragment of the sequence shown in FIG. 3 or a fragment of the sequence of substantial homology to the sequence shown in FIG. 3.

In a class of the invention is the DNA sequence which encodes a murine NPY Yx receptor.

In a subclass of the invention is the DNA sequence having a sequence selected from the sequence shown in FIG. 3, the sequence of substantial homology to the sequence shown in FIG. 3 or the fragment of the sequence shown in FIG. 3 comprising bases 822 to 1934.

In a second embodiment of the invention is the isolated DNA sequence wherein the DNA sequence has a sequence selected from a sequence as shown in FIG. 5, a sequence of substantial homology to the sequence shown in FIG. 5, a fragment of the sequence shown in FIG. 5 or a fragment of the sequence of substantial homology to the sequence shown in FIG. 5.

In a second class of the invention is the DNA sequence which encodes a human NPY Yx receptor.

In a second subclass is the DNA sequence having a sequence selected from the sequence shown in FIG. 5, the sequence of substantial homology to the sequence shown in FIG. 5 or the fragment of the sequence shown in FIG. 5 comprising bases 182 to 1291.

Illustrative of the invention is an expression vector containing any of the DNA sequences described above.

An illustration of the invention is a cell transformed by the expression vector.

Exemplifying the invention is a method of producing the neuropeptide Y Yx receptor, comprising culturing the cell under conditions which allow the production of the neuropeptide Y Yx receptor and optionally recovering the neuropeptide Y Yx receptor. An example of the invention is a neuropeptide Y Yx receptor produced by this process. Preferably, the neuropeptide Y Yx receptor produced by this process is characterized by a pharmacological binding profile with affinities of PYY≅NPY≅[Leu$^{31}$Pro$^{34}$]NPY≅NPY(2–36)>NPY(13–36). More specifically exemplifying the invention is the method wherein the cell is a mammalian cell; preferably, a COS-7 cell.

Further illustrating the invention is a neuropeptide Y Yx receptor, or a functional derivative thereof, which is characterized by a pharmacological binding profile with affinities of PYY≅NPY≅[Leu$^{31}$Pro$^{34}$]NPY≅NPY(2–36)>NPY(13–36), in substantially pure form.

More particularly illustrating the invention is an antibody immunologically reactive with the NPY Yx receptor.

Another illustration of the invention is an isolated RNA encoded by any of the DNA sequences described above or their complementary sequences.

Since a single-stranded DNA with a sequence complementary to the sequence of RNA which encodes the NPY Yx receptor could be used to modulate the expression of the receptor, another example of the invention is isolated DNA containing this complementary sequence or a fragment thereof.

Further exemplifying the invention is a neuropeptide Y Yx receptor in substantially pure form comprising an amino acid sequence selected from a sequence as shown in FIG. 3 (SEQ. I.D. NO. 6), a sequence as shown in FIG. 6 (SEQ. I.D. NO. 12), or a functional derivative thereof. Preferably, the neuropeptide Y Yx receptor has an amino acid sequence as shown in FIG. 3 (SEQ. I.D. NO. 6) or a functional derivative thereof. More preferably, the neuropeptide Y Yx receptor has an amino acid sequence as shown in FIG. 6 (SEQ. I.D. NO. 12) or a functional derivative thereof.

BRIEF DESCRIPTION OF THE DRAWINGS

FIG. 1. Schematic diagram of FRAMES analysis using the Genetics Computing Group software (Madison, Wis.) identifying a 371 amino acid open reading frame (aa ORF).

FIG. 2. Schematic diagram of hydrophobicity analysis using PEPPLOT (Genetics Computing Group software (Madison, Wis.)) indicating the open reading frame (ORF) has 7 transmembrane spanning domains characteristic of G-protein coupled receptor.

FIG. 3 shows the genomic DNA sequence and deduced amino acid sequence of the murine NPY Yx receptor. The sequence disclosure of FIG. 3 is represented as SEQ. I.D. NO. 5 and SEQ. I.D. NO. 6.

FIG. 4 shows a comparative alignment determined by BESTFIT (Genetics Computing Group software (Madison, Wis.)) of the mouse NPY Y1 receptor and the mouse NPY Yx receptor, described herein. The seven transmembrane spanning domains are indicated as are three putative N-linked glycosylation sites (indicated by a *). The sequence disclosures of the mouse NPY Y1 receptor and mouse NPY Yx receptor of FIG. 4 are represented as SEQ. I.D. NO. 7 and SEQ. I.D. NO. 6, respectively.

FIG. 5 shows the DNA sequence of the human NPY Yx receptor. The sequence disclosure of FIG. 5 is represented as SEQ. I.D. NO. 11.

FIG. 6 shows the amino acid sequence of the human NPY Yx receptor. The sequence disclosure of FIG. 6 is represented as SEQ. I.D. NO. 12.

DETAILED DESCRIPTION OF THE INVENTION

Neuropeptide Y receptors belong to a class of receptors known as "G-protein coupled receptors." The term "G-protein coupled receptor" refers to any receptor protein that mediates its endogenous signal transduction through activation of one or more guanine nucleotide binding regulatory proteins (G-proteins). These receptors share common structural features, including seven hydrophobic transmembrane domains. G-protein coupled receptors include receptors that bind to small biogenic amines, including but not limited to beta-adrenergic receptors (βAR), alpha-adrenergic receptors (αAR) and muscarinic receptors, as well as receptors whose endogenous ligands are peptides, such as neurokinin, neuropeptide Y and glucagon receptors. Examples of βAR include beta-1, beta-2, and beta-3 adrenergic receptors.

G-protein coupled receptors are cell surface proteins that mediate the responses of a cell to a variety of environmental signals. Upon binding an agonist, the receptor interacts with one or more specific G-proteins, which in turn regulate the activities of specific effector proteins. By this means, activation of G-protein coupled receptors amplifies the effects of the environmental signal and initiates a cascade of intracellular events that ultimately leads to defined cellular responses. G-protein coupled receptors function as a complex information processing network within the plasma membrane of the cell, acting to coordinate a cell's response to multiple environmental signals.

G-protein coupled receptors consist of seven hydrophobic domains connecting eight hydrophilic domains. The hydrophobicity or hydrophilicity of the domains may be determined by standard hydropathy profiles, such as Kyte-Doolittle analysis (Kyte, J. and Doolittle, R. J. F. *J. Mol. Biol.* 157:105 (1982)). The receptors are thought to be oriented in the plasma membrane of the cell such that the N-terminus of the receptor faces the extracellular space and the C-terminus of the receptor faces the cytoplasm, so that each of the hydrophobic domains crosses the plasma membrane. The receptors have been modeled and the putative boundaries of the extracellular, transmembrane and intracellular domains are generally agreed (for a review, see Baldwin, EMBO J. 12:1693, 1993 ). In general, the transmembrane domains are comprised of stretches of 20–25 amino acids in which most of the amino acid residues have hydrophobic side chains (including cysteine, methionine, phenylalanine, tyrosine, tryptophan, proline, glycine, alanine, valine, leucine, isoleucine), whereas the intracellular and extracellular loops are defined by contiguous stretches of several amino acids that have hydrophilic or polar side chains (including aspartate, glutamate, asparagine, glutamine, serine, threonine, histidine, lysine, and arginine). Polar amino acids, especially uncharged ones (such as serine, threonine, asparagine, and glutamine) are found in both transmembrane and extramembrane regions.

The present invention pertains to a novel mammalian neuropeptide Y receptor subtype (i.e., NPY Yx), particularly exemplified by the murine and human neuropeptide Y Yx receptors described in detail herein. A method of making the NPY Yx receptor is also provided. The invention includes DNA encoding the NPY Yx receptor, the NPY Yx receptor, assays employing the NPY Yx receptor, cells expressing the NPY Yx receptor, antibodies which bind specifically to the NPY Yx receptor, RNA encoded by the DNA sequence or its complementary sequence, and single-stranded DNA with a sequence complementary to the RNA which encodes the NPY Yx receptor. The NPY Yx receptor and assays employing the NPY Yx receptor are useful for identifying compounds which bind to the receptor, including specific modulators of the receptor. Modulators, as described herein, include but are not limited to agonists, antagonists, suppressors and inducers. Such modulators may be DNA, RNA, peptides, proteins, or non-proteinaceous organic molecules. Modulators identified by the processes described herein are useful as therapeutic agents. Thus, compounds identified using the mammalian NPY Yx receptor are useful for treating one or more disease conditions, including obesity, diabetes, anxiety, hypertension, cocaine withdrawal, congestive heart failure, memory enhancement, cardiac and cerebral vasospasm, pheochromocytoma and ganglioneuroblastoma, and Huntington's, Alzheimer's and Parkinson's diseases.

The receptor may include genetic variants, both natural and induced. Induced receptors may be derived by a variety of methods, including but not limited to, site-directed mutagenesis. Techniques for nucleic acid and protein manipulation are well-known in the art and are described generally in Methods in Enzymology and in Sambrook et al., Molecular Cloning: A Laboratory Manual, Cold Spring Harbor Laboratory (1989).

It is known that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate functional properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally-occurring peptide. Methods of altering the DNA sequences include, but are not limited to site directed mutagenesis. Examples of altered properties include but are not limited to changes in the affinity of an enzyme for a substrate or a receptor for a ligand.

A fragment of a DNA sequence, as used herein, refers to any polynucleotide subset of the DNA sequence or its complementary sequence. Also included within the scope of the present invention are fragments of DNA sequence capable of producing functional NPY Yx protein. An example of one such fragment capable of expressing the NPY Yx receptor protein comprises bases 822 to 1934 of the DNA sequence shown in FIG. 3. Another example of a fragment capable of expressing the NPY Yx receptor protein comprises bases 182 to 1291 of the DNA sequence shown in FIG. 5.

As used herein, a "functional derivative" of a receptor is a compound that possesses a biological activity (either functional or structural) that is substantially similar to the biological activity of the receptor. The term "functional derivative" is intended to include the "fragments," "variants," "degenerate variants," "analogs" and "homologues" or to "chemical derivatives" of the receptor. The term "fragment" is meant to refer to any polypeptide subset of receptor. The term "variant" is meant to refer to a molecule substantially similar in structure and function to either the entire receptor molecule or to a fragment thereof. A molecule is "substantially similar" to a receptor if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical.

The term "analog" refers to a molecule substantially similar in function to either the entire receptor molecule or to a fragment thereof.

The term "ligand," as used herein, refers to a molecule which binds to the receptor; the term "ligand" includes both agonists and antagonists.

"Substantial homology" or "substantial similarity," when referring to nucleic acids means that the segments or their complementary strands, when optimally aligned and compared, are identical with appropriate nucleotide insertions or deletions, in at least about 30% of the nucleotides, usually >40% of the nucleotides. Alternatively, substantial homology exists when the segments will hybridize to a strand or its complement under standard conditions. Standard hybridization conditions are described in Sambrook, J., et al., supra. Thus, the terms "substantial homology" and "substantial similarity" are intended to cover minor variation in the DNA sequence which, due to degeneracy in the DNA code, do not result in the sequence encoding a different polypeptide; further these terms are intended to cover alterations in the DNA code which lead to changes in the encoded polypeptide but in which such changes do not affect the biological activity of the peptide.

The nucleic acids claimed herein may be present in whole cells or in cell lysates or in a partially purified or substantially purified form. When referring to nucleic acids, the terms "isolated" and "substantially pure" are synonymous. A nucleic acid is considered to be isolated and/or substantially purified when it is purified away from environmental contaminants. Thus, a nucleic acid sequence isolated from cells is considered to be isolated and/or substantially purified when purified from cellular components by standard methods while a chemically synthesized nucleic acid sequence is considered to be substantially purified when purified from its chemical precursors. The term "substantially pure" is used relative to nucleic acids, proteins or peptides with which the nucleic acids of the instant invention are associated in nature, and are not intended to exclude compositions in which the nucleic acid of the invention is admixed with nonproteinous pharmaceutical carriers or vehicles.

Nucleic acid compositions of this invention may be derived from genomic DNA, cDNA, or RNA, prepared by synthesis or by a combination of techniques.

The natural or synthetic nucleic acids encoding the G-protein coupled receptor of the present invention may be incorporated into expression vectors. Usually the expression vectors incorporating the receptor will be suitable for replication in a host. Examples of acceptable hosts include, but are not limited to, prokaryotic and eukaryotic cells.

The phrase "recombinant expression system" as used herein means a substantially homogenous culture of suitable host organisms that stably carry a recombinant expression vector. Examples of suitable hosts include, but are not limited to, bacteria, yeast, fungi, insect cells, plant cells and mammalian cells. Generally, cells of the expression system are the progeny of a single ancestral transformed cell.

The cloned receptor DNA obtained through the methods described herein may be recombinantly expressed by molecular cloning into an expression vector containing a suitable promoter and other appropriate transcription regulatory elements, and transferred into prokaryotic or eukaryotic host cells to produce recombinant receptor. Techniques for such manipulations are fully described in Sambrook, J., et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, plant cells, insect cells, fungal cells and animal cells.

Specifically designed vectors allow the shuttling of DNA between hosts such as bacteria-yeast or bacteria-animal cells or bacteria-fungi or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant receptor in mammalian cells. Commercially available mammalian expression vectors which may be suitable for recombinant receptor expression, include but are not limited to, pcDNA3 (Invitrogen), pMC1neo (Stratagene), pXT1 (Stratagene), pSG5 (Stratagene), EBO-pSV2-neo (ATCC 37593) pBPV-1 (8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and λZD35 (ATCC 37565).

A variety of bacterial expression vectors may be used to express recombinant receptor in bacterial cells. Commercially available bacterial expression vectors which may be suitable for recombinant receptor expression include, but are not limited to pGEM-3ZF (Promega), pET11a (Novagen), lambda gt11 (Invitrogen), pcDNAII (Invitrogen), pKK223-3 (Pharmacia).

A variety of fungal cell expression vectors may be used to express recombinant receptor in fungal cells. Commercially available fungal cell expression vectors which may be suitable for recombinant receptor expression include but are not limited to pYES2 (Invitrogen), Pichia expression vector (Invitrogen).

A variety of insect cell expression vectors may be used to express recombinant receptor in insect cells. Commercially available insect cell expression vectors which may be suitable for recombinant expression of receptor include but are not limited to pBlue Bac III (Invitrogen).

An expression vector containing DNA encoding receptor may be used for expression of receptor in a recombinant host cell. Recombinant host cells may be prokaryotic or eukaryotic, including but not limited to bacteria such as E. coli, fungal cells such as yeast, mammalian cells including but not limited to cell lines of human, bovine, porcine, monkey and rodent origin, and insect cells including but not limited to Drosophila and silkworm derived cell lines. Cell lines derived from mammalian species which may be suitable and which are commercially available, include but are not limited to, L cells L-M(TK⁻) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171).

The expression vector may be introduced into host cells via any one of a number of techniques including but not limited to transformation, transfection, lipofection, protoplast fusion, and electroporation. The expression vector-containing cells are clonally propagated and analyzed to determine whether they produce receptor protein. Identification of receptor expressing host cell clones may be done by several means, including but not limited to immunological reactivity with anti-receptor antibodies or specific ligand binding.

Expression of receptor DNA may also be performed using in vitro produced synthetic mRNA or native mRNA. Synthetic mRNA or mRNA isolated from receptor producing cells can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

The term "substantial homology", when referring to polypeptides, indicates that the polypeptide or protein in question exhibits at least about 30% homology with the naturally occurring protein in question, usually at least about 40% homology.

The receptor may be expressed in an appropriate host cell and used to discover compounds that affect the receptor. Preferably, the receptor is expressed in a mammalian cell line, including but not limited to, COS-7, CHO or L cells, or an insect cell line, including but not limited to, Sf9 or Sf21, and may be used to discover ligands that bind to the receptor and alter or stimulate its function. The receptor may also be produced in bacterial, fungal or yeast expression systems.

The expression of the receptor may be detected by use of a radiolabeled ligand specific for the receptor. For example, for the $\beta_2$ adrenergic receptor, such a ligand may be $^{125}$I-iodocyanopindolol ($^{125}$I-Cyp). For the NPY receptor, such a ligand may be $^{125}$I-Npy or $^{125}$I-Peptide YY (PYY).

The specificity of binding of compounds showing affinity for the receptor is shown by measuring the affinity of the compounds for cells transfected with the cloned receptor or for membranes from these cells. Expression of the cloned receptor and screening for compounds that inhibit the binding of radiolabeled ligand to these cells provides a rational way for rapid selection of compounds with high affinity for the receptor. These compounds identified by the above assays may be agonists or antagonists of the receptor and may be peptides, proteins, or non-proteinaceous organic molecules. Alternatively, functional assays of the receptor may be used to screen for compounds which affect the activity of the receptor. Such functional assays range from ex vivo muscle contraction assays to assays which determine second messenger levels in cells expressing the receptor. The second messenger assays include but are not limited to assays to measure cyclic AMP or calcium levels or assays to measure adenyl cyclase activity. These compounds identified by the above assays may be agonists, antagonists, suppressors, or inducers of the receptor. The functional activity of these compounds is best assessed by using the receptor either natively expressed in tissues or cloned and exogenously expressed.

Once the receptor is cloned and expressed in a mammalian cell line, such as COS-7 cells or CHO cells, the recombinant receptor is in a well-characterized environment. The membranes from the recombinant cells expressing the receptor are then isolated according to methods known in the art. The isolated membranes or whole cells may be used in a variety of membrane-based or whole cell-based receptor binding assays. Ligands (either agonists or antagonists) may be identified by standard radioligand binding assays. These assays will measure the intrinsic affinity of the ligand for the receptor. In addition, the activity of receptor ligands or modulators of the receptor may be measured in functional assays as described above.

The present invention provides methods of identifying compounds that bind to a novel mammalian NPY Yx receptor. Methods of identifying compounds are exemplified by an assay, comprising:

a) cloning DNA which encodes a mammalian neuropeptide Y Yx receptor;

b) splicing the DNA into an expression vector to produce a construct such that the NPY Yx receptor is operably linked to transcription and translation signals sufficient to induce expression of the NPY Yx receptor upon introduction of the construct into a prokaryotic or eukaryotic cell;

c) introducing the construct into a prokaryotic or eukaryotic cell which does not express the NPY Yx receptor in the absence of the introduced construct; and d) incubating cells or membranes isolated from cells produced in step c with a quantifiable compound known to bind to the NPY Yx receptor, and subsequently adding test compounds at a range of concentrations so that the test compounds compete with the quantifiable compound for the NPY Yx receptor, such that an $IC_{50}$ for the test compound is obtained as the concentration of test compound at which 50% of the quantifiable compound becomes displaced from the NPY Yx receptor.

The present invention is also directed to methods for screening for compounds which modulate the expression of DNA or RNA encoding NPY Yx receptor or which modulate the function of NPY Yx receptor protein. Compounds which modulate these activities may be DNA, RNA, peptides, proteins, or non-proteinaceous organic molecules. Compounds may modulate by increasing or attenuating the expression of DNA or RNA encoding receptor, or the function of receptor protein. Compounds that modulate the expression of DNA or RNA encoding receptor or the function of receptor protein may be detected by a variety of assays. The assay may be a simple "yes/no" assay to determine whether there is a change in expression or function. The assay may be made quantitative by comparing the expression or function of a test sample with the levels of expression or function in a standard sample.

The present invention is also directed to methods for screening for compounds which modulate the expression of DNA or RNA encoding the NPY Yx receptor as well as the function of the NPY Yx receptor protein in vivo. Compounds which modulate these activities may be DNA, RNA, peptides, proteins, or non-proteinaceous organic molecules. Compounds may modulate by increasing or attenuating the expression of DNA or RNA encoding the receptor, or the function of the receptor protein. Compounds that modulate the expression of DNA or RNA encoding the receptor or the function of the receptor protein may be detected by a variety of assays. The assay may be a simple "yes/no" assay to determine whether there is a change in expression or function. The assay may be made quantitative by comparing the expression or function of a test sample with the levels of expression or function in a standard sample.

Kits containing receptor DNA, antibodies to receptor, or receptor protein may be prepared. Such kits are used to detect DNA which hybridizes to receptor DNA or to detect the presence of receptor protein or peptide fragments in a sample. Such characterization is useful for a variety of purposes including but not limited to forensic, taxonomic or epidemiological studies.

The DNA molecules, RNA molecules, recombinant protein and antibodies of the present invention may be used to screen and measure levels of receptor DNA, receptor RNA or receptor protein. The recombinant proteins, DNA molecules, RNA molecules and antibodies lend themselves to the formulation of kits suitable for the detection and typing of receptor. Such a kit would comprise a compartmentalized carrier suitable to hold in close confinement at least one container. The carrier would further comprise reagents such as recombinant receptor protein or anti-receptor antibodies suitable for detecting receptor. The carrier may also contain a means for detection such as labeled antigen or enzyme substrates or the like.

Compounds identified by the screening methods identified herein are formulated into pharmaceutical compositions according to standard methods. The compounds or pharmaceutical compositions are used either alone or in combination with other compounds or compositions for the treatment of animals (including humans) in need of treatment. Conditions which can be treated with compounds identified by the methods of the present invention include but are not limited to obesity, regulation of appetite, congestive heart failure, diabetes, anxiety, hypertension, cocaine withdrawal, congestive heart failure, memory enhancement, cardiac and cerebral vasospasm, pheochromocytoma and ganglioneuroblastoma, and Huntington's, Alzheimer's and Parkinson's diseases. Thus, animals (including humans) having a condition, the condition being characterized by factors selected from altered levels of neuropeptide Y, altered activities of neuropeptide Y, altered levels of neuropeptide Y receptor activity, altered neuropeptide Y receptor activity, and combinations thereof, can be treated with compounds or derivatives of compounds (or pharmaceutical compositions comprising the compounds or derivatives of compounds) identified by the screening methods described herein.

Pharmaceutically useful compositions comprising modulators of receptor activity, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain a pharmacologically effective amount of the protein, DNA, RNA, or modulator. The term "pharmacologically effective amount," as used herein, means that amount of a drug or pharmaceutical agent that will elicit the biological or medical response that is being sought by a researcher or clinician.

Therapeutic or diagnostic compositions of the invention are administered to an individual in amounts sufficient to treat or diagnose disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

The terms "derivative" or "chemical derivative" describe a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages. Alternatively, co-administration or sequential administration of other agents may be desirable.

The present invention also has the objective of providing suitable topical, oral, systemic and parenteral pharmaceutical formulations for use in the novel methods of treatment of the present invention. The compositions containing compounds identified according to this invention as the active ingredient can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

Advantageously, compounds identified by the methods of the present invention may be administered in a single daily dose, or the total daily dosage may be administered in divided doses of two, three or four times daily. Furthermore, these compounds can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

The following examples are provided to further define the invention without, however, limiting the invention to the particulars of the examples.

EXAMPLE 1

Genomic DNA Cloning of a NPY Yx Receptor

A mouse genomic DNA library was constructed using published procedures (Mudgett, J. S. and Macinnes, M. A. *Genomics* 8, 623–633(1990)) in the cosmid sCOS vector using genomic DNA isolated from the embryonic stem cell line J 1 (ES-J 1 ) (Dr. R. Jaenisch, The Whitehead Institute) which was derived from J 129 SV mice (J. Mudgett, MRL). The recombinant DNA library constructed from genomic DNA of ES-J 1 cells was plated on Colony/Plaque screen hybridization transfer membrane (Dupont/NEN) at a density of approximately 30,000 colonies per plate. Alternatively, ES-14TG2A mouse pluripotent stem cells (ATCC CRL1821) can be used in place of the ES-J1 stem cell line. Replicas of master plates were lysed and processed for hybridization using standard protocols (Sambrook, J., Fritsch, E. F., Maniatis, T. in Molecular Cloning: A Laboratory Manual, Second Edition, Cold Spring Harbor Laboratory, Cold Spring Harbor, N.Y., 1989). The DNA was UV crosslinked to the membrane with a Stratalinker (Stratagene). The filters were incubated overnight at 42° C. with radiolabeled probe in 35% formamide hybridization solution, [5 x SSC, 0.02% SDS, 0.1% n-lauroyl sarcosine, 0.02% (w/v) blocking buffer (Boehringer Mannheim Biochemicals)]. The probe, a DNA fragment containing coding sequences of the human Y1 neuropeptide Y receptor from transmembrane domains 3 to 7, was generated by PCR (Perkin Elmer Cetus) using primers 554 (5' CACTGGGTCTTTGGTGAGGCGATGTG 3') (SEQ. I.D. NO. 1 ) and 1300 (5' CCCATAAAATATGGGGTTGACA-CAAGTGG 3') (SEQ. I.D. NO. 2) with human Y1 cDNA as template and in the presence of [$\alpha$-$^{32}$P] dCTP (deoxycytidinetriphosphate) (3000 Ci/mmole). Filters were washed at a final stringency of 0.5 x SSC, 0.1% SDS at 42° C. Positives were rescreened to isolate single colonies. DNA was prepared from positive colonies, digested with restriction enzymes, and Southern blot analysis was done to identify restriction fragments for subcloning. A fragment identified by this hybridization was subcloned into pGEM-3ZF (Promega).

EXAMPLE 2

Isolation of ET15952 (pVE2841 )

Filters containing PstI fragments cloned from the mouse cosmid library were hybridized to a human NPY Y 1 receptor cDNA probe. The probe was prepared using a PCR labeling kit (Bethesda Research Labs, Bethesda, Md.). The forward primer was (5' TTGGCCATGATATTTACCT-TAGCT 3') (SEQ. I.D. NO. 3), the reverse primer was (5' GCATCAAGTGTTACATTTTGGAAC 3') (SEQ. I.D. NO. 4), and the template was a 928 bp EcoRI-EcoRV restriction fragment prepared with Qiaex resin (Qiagen Inc., Chatsworth, Calif.) from an agarose gel slice of restricted and electrophoresed NPY Y1 cDNA. The PCR product was a 463 bp fragment spanning transmembrane domains 1 to 4 of the NPY Y1 receptor. Hybridization was performed using prehybridization and hybridization solutions (5 Prime →3 Prime, Inc., Boulder, Colo.) with an Autoblot oven and bottles (Bellco Glass Co., Vineland, N.J.). After a prehybridization at 60° C. for 3 hrs, 2×10$^7$ CPM of the heat denatured probe was added to each hybridization bottle and the filters were hybridized at 60° C. for 1 hr, then 55° C. for 11 hrs, and 50° C. for 3 hrs. After hybridization, the filters were washed in 2 X SSC, 0.1% SDS, first at room temperature for 60 min, then at 30° C. for 20 min, then at 45° C. for 30 min and the filters were then exposed to Kodak X-OMAT AR film for 4 hrs. Several putative hybridizing colonies were identified and DNA was purified from these clones by Qiaprep system (Qiagen, Inc., Chatsworth, Calif.), subjected to digestion with EcoR1 and EcoRV, separated by electrophoresis in an agarose gel, and transferred to a nylon filter (Zeta-Probe, Bio-Rad Laboratories, Hercules, Calif.) using the Stratagene Posiblot system. The resulting filters were hybridized to the PCR labeled 463 bp NPY Y1 receptor cDNA fragment as described above. After a final stringent wash at 55° C. for 45 min in 2 X SSC, 0.1 SDS the filters were then exposed to Kodak X-OMAT AR film for 1 hr. One hybridizing clone, designated ET15952 and containing plasmid pVE284 1, was selected for DNA sequence analysis.

EXAMPLE 3

Sequence Analysis of pVE2841

DNA was prepared from overnight cultures of ET15952 using the Wizard DNA Purification System (Promega Corp., Madison, Wis.) and subjected to automated sequence analysis using the PRISM Dye Deoxy terminator cycle sequencing kit (Applied Biosystems, Foster City, Calif.). Initial sequencing primers were complementary to the T7 and SP6 promoter sites in pGEM 3ZF, additional primers were made complementary to the insert DNA in pVE2841. Sequencing indicated that pVE2841 contains a 2280 bp PstI insert. FRAMES analysis using the Genetics Computing Group software (Madison, Wis.) identified a 371 amino acid open reading frame (FIG. 1). Hydrophobicity analysis using PEPPLOT (Genetics Computing Group software (Madison, Wis.)) indicates the open reading frame has 7 hydrophobic domains characteristic of the transmembrane spanning domains of G-protein coupled receptors (FIG. 2). The DNA sequence of the PstI fragment and the region encoding the open reading frame are shown in FIG. 3. The DNA encoding the open reading frame appears to lack introns and is 59% identical to mouse NPY Y1 receptor cDNA, while the codon sequence of the open reading frame is 52% identical to the mouse NPY Y1 receptor. A comparative alignment determined by BESTFIT (Genetics Computing Group software (Madison, Wis.)) of the mouse NPY Y1 receptor and the novel homolog described herein is presented in FIG. 4. In FIG. 4 the seven potential transmembrane spanning domains are indicated as are three putative N-linked glycosylation sites (indicated by a *).

EXAMPLE 4

Construction of a Vector for Expression of the murine NPY Yx Receptor DNA in Mammalian Cells 3 µg of pcDNA3 DNA (Invitrogen Corp., San Diego, Calif.) was digested with restriction enzyme EcoRV according to the manufacturer's directions (Bethesda Research Labs, Bethesda, Md.) in a reaction mixture of 40 µl. After 2 hours of digestion at 37° C., the 5' ends of the vector were dephosphorylated by adding 2 µl of an alkaline phosphatase solution (Boehringer Mannheim, Indianapolis, Ind.) (0.1 U in 10 mM Tris pH7, 10 mM $MgCl_2$, 0.1 mM $ZnCl_2$, 50% glycerol) and incubating at 37° C. After an hour, the enzymes were heat inactivated at 65° C. for 10 min. 5 µg of pVE2841 were digested with restriction enzyme PstI, according to the manufacture's directions (Bethesda Research Labs, Bethesda, Md.), in a 40 µL solution. The 3' overhanging ends of the 2.3 kb PstI fragment were convened to blunt ends by adding 8.8 µL of 5x T4 DNA Polymerase buffer and 5 U of T4 DNA polymerase (Bethesda Research Labs, Bethesda, Md.) and continuing the incubation at 37° C. After an hour, the enzymes were heat inactivated at 65° C. for 10 min. The reaction products were separated on a 1% agarose gel (Sigma Chemical Co., St. Louis, Miss.) and the cleaved pcDNA3 vector and 2.3 kb fragment were purified from the agarose gel using Qiaex resin (Qiagen Corp., Chatsworth, Calif.). The purified DNA fragments were resuspended in 25 µL of TE (10 mM Tris pH 7.4, 1 mM EDTA). The 2.3 kb fragment was ligated to the pcDNA3 vector DNA in a 20 µL reaction containing 1 µL of purified vector, 3 µL of purified 2.3 kb fragment, 4 µL of 5x T4 DNA ligation buffer (Bethesda Research Labs, Bethesda, Md.), 11 µL of water, and 1 µl of T4 DNA ligase (1 U, Bethesda Research Labs, Bethesda, Md.). After ligation for 2 hr at 20° C., 1 µL of the ligation mixture was transformed into 20 µL of XL1Blue competent E. coli cells (Stratagene, La Jolla, Calif.), according to the manufacturer's directions. Transformants were isolated as ampicillin-resistant colonies and plasmid DNA was isolated from transformants by Qiaprep system (Qiagen Corp. Chatsworth, Calif.). Among the transformants containing the 2.3 kb insert, one isolate was identified and designated pVE2863 which contained the 2.3 kb in the correct orientation for expression from the CMV promoter.

EXAMPLE 5

Pharmacology of the Recombinant NPY Yx Receptor

Using electroporation, COS-7 cells were transfected with the pcDNA3 expression vector containing the genomic DNA for the murine NPY Yx receptor (pVE2863). Two days post transfection, cells were dissociated with enzyme-free dissociation buffer, centrifuged at 1000 rpm for 10 minutes at 4° C., and resuspended in 10 mM Tris, pH 7.4 containing 0.1 M PMSF (phenylmethylsulfonyl fluoride), 10 µM phosphoramidon, and 40 µg/ml bacitracin. The cell suspension was homogenized with a glass homogenizer, and centrifuged at 2200 rpm for 10 minutes at 4° C. to remove cell debris. The plasma membrane fraction was recovered by centrifuging the supernatant at 18,000 rpm in a Sorvall SS-34 rotor for 15 minutes at 4° C. The membrane pellet was resuspended in the Tris/PMSF/phosphoramidon/bacitracin buffer by trituration 5 times using a 25 g needle and syringe. The membranes were stored frozen at −80° C. until use.

Membranes (50 µg protein) were incubated with $^{125}$I-PYY (90 pM) in the presence or absence of 1 µM unlabeled PYY (non-specific binding) or serial dilutions of other competing peptides in 0.25 ml of 50 mM Tris, pH 7.4 containing 2 mM $CaCl_2$, 1 mM $MgCl_2$, 5 mM KCl, 0.2% bovine serum albumin, 10 µM phosphoramidon, 4 µg/ml leupeptin and 40 µg/ml bacitracin. After 2 hours at room temperature, the incubation was filtered over GF/C filters, and the radioactivity bound to the filters was quantified with a Packard gamma counter. The percentage of inhibition of $^{125}$I-PYY binding at a given concentration of competing peptide was plotted versus the concentration of peptide added, and the concentration of peptide causing 50% inhibition of binding ($IC_{50}$) was determined using non-linear regression performed by PRISM (GraphPad).

| Competitor | IC$_{50}$ (nM) |
| --- | --- |
| PYY | 14 |
| NPY | 6 |
| [Leu$^{31}$, Pro$^{34}$]NPY | 9 |
| NPY$_{(2-36)}$ | 16 |
| NPY$_{(13-36)}$ | 134 |

EXAMPLE 6

Human NPY Yx Receptor

Isolation of the hybridization probe. A hybridization probe with identity to the human NPY Yx receptor was generated by PCR using human genomic DNA as the target. Oligonucleotide primer pairs based upon the DNA sequence of the mouse NPY Yx receptor (primer 1; 5'ACCAGTG-GCAAGAGCAACAAC (SEQ. I.D. NO. 8), primer 2; 5'CTCATTGGTGAGGTGGTAGGAC (SEQ. I.D. NO. 9)) were used in a primary PCR reaction. The products of this reaction were used as the template for a second PCR reaction using primer 2 and primer 3 (5'.GGGCATTTTTGGAAAC-CTCTC (SEQ. I.D. NO. 10)). Primer 3, a 'nested' primer, was designed to hybridize to mouse NPY Yx receptor sequences which are internal to those with homology to primers 1 and 2. A product obtained from the second PCR reaction was cloned and found to share homology to the mouse NPY Yx receptor by DNA sequence analysis in both directions using an ABI 373A automated sequencing unit (Perkin Elmer).

Isolation of a human NPY Yx receptor cDNA clone. A commercial lambda phage library (Lambda Zap2, Stratagene) containing cDNAs derived from human heart mRNA was screened. Approximately 1×10$^6$ plaques were plated at a density of 50,000 plaques per 150 mm plate and transferred to Colony/Plaque screen hybridization membranes (Dupont/NEN) which were then processed by standard protocols (as supplied by Stratagene). DNA was UV crosslinked to the membrane with a Stratalinker (Stratagene). The filters were prewashed with 500 mls of 0.1X SSC, 0.1% SDS at 65° C. for 1 hour and then prehybridized in a solution of 0.25M NaPO$_4$, 7% SDS pH7.5 at 60° C. for 1 hour. The PCR fragment having identity to the human NPY Yx receptor described above was labeled by random priming (Rediprime, Amersham) in the presence of [α-$^{32}$P] dCTP (3000 Ci/mmole). The membranes were allowed to hybridize to the [α-$^{32}$P]-labeled PCR fragment in a solution of 0.25M NaPO$_4$, 7% SDS, 10% dextran sulfate pH7.5 for 16 hours at 60° C. The membranes were washed in 1 liter of 1X SSC, 0.1% SDS at 45° C. and then exposed to Kodak XAR-5 Xray film. Primary positives identified by this procedure were selected, re-plated, and subjected to a second round of hybridization screening to allow identification and selection of individual hybridization positive plaques. Plasmids containing the cDNA inserts were rescued from the phage using methodology supplied by the manufacturer (Stratagene) which results in the generation of bacterial colonies. Bacterial colonies with plasmids containing the human NPY Yx receptor cDNA sequences were identified by filter hybridization with the [α-$^{32}$P]-labeled human NPY Yx receptor probe using standard methodologies (Sambrook, J., Fritsch, E. F., Maniatis, T. in Molecular Cloning: A Laboratory Manual, Second Edition, Cold Spring Harbor Laboratory, Cold Spring Harbor, N.Y. 1989). The cloned cDNA, pCD13, was analyzed by sequencing in both directions using an ABI 373A automated sequencing unit (Perkin Elmer).

Structure of the human NPY Yx receptor cDNA. The DNA sequence of the approximately 1499 bp clone of human NPY Yx receptor cDNA, pCD 13 (SEQ. I.D. NO. 11) contains an open reading frame of about 1110 bp. The proposed initiator methionine at nucleotide 182 conforms to the Kozak sequence (M. Kozak, Journal of Cell Biology 108, 229–241 (1989)) at the +4 position but not at the −3 position. The proposed 370 amino acid sequence (SEQ. I.D. NO. 12) encoded by the open reading frame is 82% identical to the amino acid sequence encoded by the open reading frame of the mouse NPY Yx receptor clone. The human NPY Yx receptor cDNA is 78% identical to the DNA of the mouse NPY Yx receptor. The human NPY Yx receptor cDNA described herein contains 181 untranslated nucleotides at the 5 prime end and 208 nucleotides following the stop codon.

EXAMPLE 7

Construction of a Vector for Expression of the Human NPY Yx Receptor DNA in Mammalian Cells 2 µg of pcDNA3 DNA (Invitrogen Corp., San Diego, Calif.) was digested with restriction enzyme EcoRI according to the manufacturer's directions (Bethesda Research Labs, Bethesda, Md.) in a reaction mixture of 20 µl. The DNA was resolved by electrophoresis on a 1% agarose gel (Sigma Chemical Co., St. Louis Miss.) and the linearized vector was identified and excised from the gel. The DNA was purified by Gene Clean using the procedure supplied by the manufacturer (BIO 101 Inc., Vista, Calif.). The 5' ends of the vector were dephosphorylated by adding 1 µl (0.1 unit) of an alkaline phosphatase solution (Boehringer Mannheim, Indianapolis, Ind.) in 50 µl of 10 mM Tris pH7, 10 mM MgCl$_2$, 0.1 mM ZnCl$_2$, 50% glycerol and incubating at 37° C. for 1 hour. The DNA was subjected to a second round of Gene Clean purification and resuspended in 50 µl of TE (10 mM Tris pH 7.4, 1 mM EDTA). Approximately 2 µg of an isolated human NPYx receptor clone, pCD 13, was digested with restriction enzyme Eco RI (Bethesda Research Labs, Bethesda, Md.) in a 20 µl solution. The reaction products were resolved by electrophoresis on a 1% agarose gel and the approximately 1.6 kb fragment containing the receptor coding sequences was purified by Gene Clean as above and resuspended in 50 µl of TE. The 1.6 kb fragment was ligated to the linearized pcDNA3 vector DNA in a 10 µl reaction containing 1 µl of purified vector, 3 µl of purified 1.6 kb fragment, 1 µl of 10x T4 DNA ligation buffer (Boehringer Mannheim, Indianapolis, Ind.), 5 µl of water, and 1 µl of T4 DNA ligase (1 U, Boehringer Mannheim, Indianapolis, Ind.). After ligation for 2 hr at 20° C., 1 µl of the ligation mixture was transformed into 50 µl of Max Efficiency DH5alpha competent E. coli cells (Bethesda Research Labs, Bethesda, Md.), according to the manufacturer's directions. Transformants were isolated as ampicillin-resistant colonies and plasmid DNA was isolated from transformants using the WIZARD miniprep system (Promega Corporation, Madison Wis.). Among the transformants containing the 1.6 kb insert, one isolate was identified and designated pcDNA3HYx-RI, which contained the 1.6 kb in the correct orientation for expression from the CMV promoter.

In an analagous fashion, 2 µg of pcDNA3 DNA (Invitrogen Corp., San Diego, Calif.) was digested with restriction enzymes EcoRI and Hind III according to the manufacturer's directions (Bethesda Research Labs, Bethesda, Md.) in a reaction mixture of 20 µl. The large fragment of doubly digested vector was purified by Gene Clean and resuspended in 50 µl of TE. Approximately 2 µg of one of the isolated human NPYx receptor clones, pCD 13, was digested with restriction enzymesEco RI and Hind III according to the manufacturer's directions (Bethesda Research Labs, Bethesda, Md.) in a 20 µl reaction. The approximately 1.6 kb fragment containing the receptor coding sequences was purified by Gene Clean and resuspended in 50 µl of TE. The 1.6 kb fragment was ligated to the pcDNA3 vector DNA in a 10 µl reaction containing 1 µl of purified vector, 3 µl of purified 1.6 kb fragment, 1 µl of 10x T4 DNA ligation buffer (Boehringer Mannheim, Indianapolis, Ind.), 5 µl of water, and 1 µl of T4 DNA ligase (1 U, Boehringer Mannheim, Indianapolis, Ind.). After ligation for 2 hr at 20° C., 1 µl of the ligation mixture was transformed into 50 µl of Max Efficiency DH5alpha competent *E. coli* cells (Bethesda Research Labs, Bethesda, Md.), according to the manufacturer's directions. Transformants were isolated as ampicillin-resistant colonies and plasmid DNA was isolated from transformants using the WIZARD miniprep system (Promega Corporation, Madison Wis.). Among the transformants containing the 1.6 kb insert, one isolate was identified and designated pcDNA3HYx-Hind/RI, which contained the 1.6 kb in the correct orientation for expression from the CMV promoter. The two expression constructs, pcDNA3HYx-RI and pcDNA3HYx-Hind/RI, differ in the amount of cDNA sequences 5 prime to the ATG translational start codon which remain in the final expression construct.

EXAMPLE 8

Cloning and Expression of NPY Yx Receptor DNA into Bacterial Expression Vectors

Recombinant receptor is produced in a bacterial expression system such as *E. coli*. The receptor expression cassette is transferred into an *E. coli* expression vector; expression vectors include but are not limited to, the pET series (Novagen). The pET vectors place receptor expression under control of the tightly regulated bacteriophage T7 promoter. Following transfer of this construct into an *E. coli* host which contains a chromosomal copy of the T7 RNA polymerase gene driven by the inducible lac promoter, expression of receptor is induced by addition of an appropriate lac substrate (IPTG) added to the culture. The levels of expressed receptor are determined by the assays described herein.

EXAMPLE 9

Cloning and Expression of NPY Yx Receptor DNA into a Vector for Expression in Insect Cells Baculovirus vectors derived from the genome of the AcNPV virus are designed to provide high level expression of DNA in the Sf9 line of insect cells (ATCC CRL# 1711). Recombinant baculovirus expressing receptor DNA is produced by the following standard methods (InVitrogen Maxbac Manual): the receptor DNA constructs are ligated into the polyhedrin gene in a variety of baculovirus transfer vectors, including the pAC360 and the BlueBac vector (InVitrogen). Recombinant baculoviruses are generated by homologous recombination following co-transfection of the baculovirus transfer vector and linearized AcNPV genomic DNA [Kitts, P. A., *Nuc. Acid. Res.* 18, 5667 (1990)] into Sf9 cells. Recombinant pAC360 viruses are identified by the absence of inclusion bodies in infected cells and recombinant pBlueBac viruses are identified on the basis of β-galactosidase expression (Summers, M. D. and Smith, G. E., Texas Agriculture Exp. Station Bulletin No. 1555). Following plaque purification, receptor expression is measured by assays described herein.

Authentic receptor is found in association with the infected cells. Active receptor is extracted from infected cells by hypotonic or detergent lysis.

Alternatively, the receptor is expressed in the Drosophila Schneider 2 cell line by cotransfection of the Schneider 2 cells with a vector containing the receptor DNA downstream and under control of an inducible metallothionin promoter, and a vector encoding the G418 resistant neomycin gene. Following growth in the presence of G418, resistant cells are obtained and induced to express receptor by the addition of $CuSO_4$. Identification of modulators of the receptor is accomplished by assays using either whole cells or membrane preparations.

EXAMPLE 10

Cloning of NPY Yx Receptor DNA into a Yeast Expression Vector

Recombinant receptor is produced in the yeast *S. cerevisiae* following the insertion of the receptor DNA cistron into expression vectors designed to direct the intracellular or extracellular expression of heterologous proteins. In the case of intracellular expression, vectors such as EmBLyex4 or the like are ligated to the receptor cistron [Rinas, U. et al., *Biotechnology* 8, 543–545 (1990); Horowitz B. et al., *J. Biol. Chem.* 265, 4189–4192 (1989)]. For extracellular expression, the receptor cistron is ligated into yeast expression vectors which fuse a secretion signal. The levels of expressed receptor are determined by the assays described herein.

EXAMPLE 11

Purification of Recombinant NPY Yx Receptor

Recombinantly produced receptor may be purified by a variety of procedures, including but not limited to antibody affinity chromatography.

Receptor antibody affinity columns are made by adding the anti-receptor antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) together with appropriate membrane solubilizing agents such as detergents, and the cell culture supernatants or cell extracts containing solubilized receptor or receptor subunits are slowly passed through the column. The column is then washed with phosphate-buffered saline (PBS) supplemented with detergents until the optical density (A280) falls to background; then the protein is eluted with 0.23M glycine-HCl (pH 2.6) supplemented with detergents. The purified receptor protein is then dialyzed against PBS.

EXAMPLE 12

Screening Assays

Recombinant cells containing DNA encoding the novel murine or human NPY Yx receptor, membranes derived from the recombinant cells, or recombinant receptor preparations derived from the cells or membranes may be used to identify compounds that modulate the murine or human NPY Yx receptor activity. Modulation of such activity may occur at the level of DNA, RNA, protein or combinations thereof. One method of identifying compounds that modulate NPY Yx receptor activity or modulate binding of ligands to the protein, comprises:

(a) mixing a test compound with a solution containing NPY Yx receptor, or a functional derivative thereof, to form a mixture;

(b) measuring NPY Yx receptor activity in the mixture; and (c) comparing the NPY Yx receptor activity of the mixture to a standard. Preferably, the neuropeptide Y Yx receptor, or functional derivative thereof, is characterized by a pharmacological binding profile with affinities of PYY≅NPY≅[Leu$^{31}$Pro$^{34}$]NPY≅NPY(2–36)>NPY(13–36).

This screening assay will detect a compound that has affinity for the NPY Yx receptor. Such compounds may be either agonists or antagonists and may be peptides, proteins, or non-proteinaceous organic molecules.

Another method of identifying compounds that modulate the NPY Yx receptor, comprises:

(a) mixing a test compound with cells which express the NPY Yx receptor to form a mixture;

(b) culturing the cells in the presence of the test compound;

(c) measuring NPY Yx receptor or second messenger activity in the mixture; and (d) comparing the NPY Yx receptor activity of the mixture to a standard. In a preferred embodiment, the cells are transformed by an expression vector containing a sequence selected from a sequence as shown in FIG. 3, a sequence of substantial homology to the sequence shown in FIG. 3, a fragment of the sequence shown in FIG. 3, a fragment of the sequence of substantial homology to the sequence shown in FIG. 3, a sequence as shown in FIG. 5, a sequence of substantial homology to the sequence shown in FIG. 5, a fragment of the sequence shown in FIG. 5 or a fragment of the sequence of substantial homology to the sequence shown in FIG. 5.

In one example of the method, the expression vector contains a DNA sequence selected from a DNA sequence having a sequence selected from a sequence as shown in FIG. 3 a sequence of substantial homology to the sequence shown in FIG. 3, a fragment of the sequence shown in FIG. 3 or a fragment of the sequence of substantial homology to the sequence shown in FIG. 3. Preferably, the expression vector contains a DNA sequence selected from the sequence shown in FIG. 3, the sequence of substantial homology to the sequence shown in FIG. 3 or the fragment of the sequence shown in FIG. 3 comprising bases 822 to 1934.

In another example of the method, the expression vector contains a DNA sequence selected from a DNA sequence having a sequence selected from a sequence as shown in FIG. 5, a sequence of substantial homology to the sequence shown in FIG. 5, a fragment of the sequence shown in FIG. 5 or a fragment of the sequence of substantial homology to the sequence shown in FIG. 5. Preferably, the expression vector contains a DNA sequence selected from the sequence shown in FIG. 5, the sequence of substantial homology to the sequence shown in FIG. 5 or the fragment of the sequence shown in FIG. 5 comprising bases 182 to 1291.

This screening assay will detect a compound which modulates NPY Yx receptor activity. Such compounds may be either agonists, antagonists, suppressors or inducers. Such compounds may be DNA, RNA, peptides, proteins, or non-proteinaceous organic molecules.

While the invention has been described and illustrated with reference to certain preferred embodiments thereof, those skilled in the art will appreciate that various Changes, modifications and substitutions can be made therein without departing from the spirit and scope of the invention. It is intended, therefore, that the invention be limited only by the scope of the claims which follow and that such claims be interpreted as broadly as is reasonable.

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:1:

```
CACTGGGTCT  TTGGTGAGGC  GATGTG                                    2 6
```

( 2 ) INFORMATION FOR SEQ ID NO:2:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:2:

CCCATAAAAT ATGGGGTTGA CACAAGTGG 29

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:3:

TTGGCCATGA TATTTACCTT AGCT 24

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:4:

GCATCAAGTG TTACATTTTG GAAC 24

( 2 ) INFORMATION FOR SEQ ID NO:5:

( i ) SEQUENCE CHARACTERISTICS:
        ( A ) LENGTH: 2280 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 822..1937

( x i ) SEQUENCE DESCRIPTION: SEQ ID NO:5:

```
CTGCAGTCTA TTGGATGAAG AGTGTACATA TTCATATAAT TCTTAAAGTA GGCAGAAATT      60
AAAGGGGATG GAAATATATA CTTGTACTGC CTTAGATAGT CACCAGGATG TTGTTACAGT     120
CTTCGTTTAC TGCTTCTGAA GCCTATACTG ATAGAATTAA TAAATACTG  AGAGAGAG      180
AGAGGGACAG AGAGAGAGAG GGGGAGAGAG AGAGAGAGAG AGAGAGAGAG AGAGAGAGAG     240
AGAGAGAGAG AGAAGAGAAG AAAACAAGGT AAGCCATCTG CTTAACTTAT GTCCACATTC     300
TCTCAAGAGC ATTGTCCTAT TTGTAGAATT ATCTATATTG TTAAGAATCA TCTCCATTGT     360
TAAGATTTTG TGGGCTGGAG ATCCAGCTCT GTTGATAAAG TGCTTGCCTA ACATGCATGA     420
AGTCCTAGGT TCTATTCCCA AGGCTACATA AAACCTTGTG TTGTGATGAA TGCCTGTAAT     480
CCCAGTACGC AGCAAGGAGA GACAAGGAGG ATCAGAAGCT TAAGGACATC ATTTTGTACA     540
TAGTGAGTTT GAGGAAAGCT GAGGTTACAT GGAACTCTCT CTCTCTCAAA AACAAAACAA     600
```

```
AACAAAACAA AACCTTCTAC TAATATTCTG GATTCTGTTT GATTTTTAGG ATCTCAAGAG    660

CATGCTGACG TCATTTATGT GTTTCCATCA GATACAGACA GAGATCATAA ACATTTAACT    720

CATTGATTAT ATGTTGAGAG TTGTCCCTCA AGAACCAATG GCCAAACATC CACTGAGGAT    780

ACACGGAAGC TTAGAAAATC TCTAATTAAA ATCCTGACAT A ATG GAA GTG CTC        833
                                              Met Glu Val Leu
                                              1
```

| ACA | AAC | CAG | CCA | ACA | CCT | AAT | AAA | ACC | AGT | GGC | AAG | AGC | AAC | AAC | TCG | 881 |
|---|---|---|---|---|---|---|---|---|---|---|---|---|---|---|---|---|
| Thr | Asn | Gln | Pro | Thr | Pro | Asn | Lys | Thr | Ser | Gly | Lys | Ser | Asn | Asn | Ser | |
| 5 | | | | 10 | | | | | 15 | | | | | | 20 | |

| GCA | TTT | TTC | TAC | TTT | GAA | TCC | TGC | CAA | CCC | CCT | TTT | CTA | GCC | ATA | CTC | 929 |
|---|---|---|---|---|---|---|---|---|---|---|---|---|---|---|---|---|
| Ala | Phe | Phe | Tyr | Phe | Glu | Ser | Cys | Gln | Pro | Pro | Phe | Leu | Ala | Ile | Leu | |
| | | | | 25 | | | | | 30 | | | | | 35 | | |

| TTG | CTA | CTC | ATA | GCA | TAT | ACT | GTG | ATC | CTA | ATC | ATG | GGC | ATT | TTT | GGA | 977 |
|---|---|---|---|---|---|---|---|---|---|---|---|---|---|---|---|---|
| Leu | Leu | Leu | Ile | Ala | Tyr | Thr | Val | Ile | Leu | Ile | Met | Gly | Ile | Phe | Gly | |
| | | | 40 | | | | | 45 | | | | | 50 | | | |

| AAC | CTC | TCT | CTT | ATC | ATC | ATC | ATC | TTT | AAG | AAA | CAG | AGA | GAA | GCT | CAA | 1025 |
|---|---|---|---|---|---|---|---|---|---|---|---|---|---|---|---|---|
| Asn | Leu | Ser | Leu | Ile | Ile | Ile | Ile | Phe | Lys | Lys | Gln | Arg | Glu | Ala | Gln | |
| | | 55 | | | | | 60 | | | | | 65 | | | | |

| AAT | GTT | ACC | AAC | ATA | CTG | ATT | GCC | AAC | CTG | TCC | CTC | TCT | GAC | ATC | TTG | 1073 |
|---|---|---|---|---|---|---|---|---|---|---|---|---|---|---|---|---|
| Asn | Val | Thr | Asn | Ile | Leu | Ile | Ala | Asn | Leu | Ser | Leu | Ser | Asp | Ile | Leu | |
| | 70 | | | | | 75 | | | | | 80 | | | | | |

| GTG | TGT | GTC | ATG | TGC | ATC | CCT | TTT | ACG | GTC | ATC | TAC | ACT | CTG | ATG | GAC | 1121 |
|---|---|---|---|---|---|---|---|---|---|---|---|---|---|---|---|---|
| Val | Cys | Val | Met | Cys | Ile | Pro | Phe | Thr | Val | Ile | Tyr | Thr | Leu | Met | Asp | |
| 85 | | | | | 90 | | | | | 95 | | | | | 100 | |

| CAC | TGG | GTA | TTT | GGG | AAC | ACT | ATG | TGT | AAA | CTC | ACT | TCC | TAC | GTG | CAA | 1169 |
|---|---|---|---|---|---|---|---|---|---|---|---|---|---|---|---|---|
| His | Trp | Val | Phe | Gly | Asn | Thr | Met | Cys | Lys | Leu | Thr | Ser | Tyr | Val | Gln | |
| | | | | 105 | | | | | 110 | | | | | 115 | | |

| AGT | GTC | TCA | GTT | TCT | GTG | TCC | ATA | TTC | TCC | CTT | GTG | TTG | ATT | GCT | ATT | 1217 |
|---|---|---|---|---|---|---|---|---|---|---|---|---|---|---|---|---|
| Ser | Val | Ser | Val | Ser | Val | Ser | Ile | Phe | Ser | Leu | Val | Leu | Ile | Ala | Ile | |
| | | | 120 | | | | | 125 | | | | | 130 | | | |

| GAA | CGA | TAT | CAG | CTG | ATT | GTG | AAC | CCC | CGT | GGC | TGG | AAA | CCC | AGA | GTA | 1265 |
|---|---|---|---|---|---|---|---|---|---|---|---|---|---|---|---|---|
| Glu | Arg | Tyr | Gln | Leu | Ile | Val | Asn | Pro | Arg | Gly | Trp | Lys | Pro | Arg | Val | |
| | | 135 | | | | | 140 | | | | | 145 | | | | |

| GCT | CAT | GCC | TAT | TGG | GGG | ATC | ATC | TTG | ATT | TGG | CTC | ATT | TCT | CTG | ACA | 1313 |
|---|---|---|---|---|---|---|---|---|---|---|---|---|---|---|---|---|
| Ala | His | Ala | Tyr | Trp | Gly | Ile | Ile | Leu | Ile | Trp | Leu | Ile | Ser | Leu | Thr | |
| | 150 | | | | | 155 | | | | | 160 | | | | | |

| TTG | TCT | ATT | CCC | TTA | TTC | CTG | TCC | TAC | CAC | CTC | ACC | AAT | GAG | CCC | TTT | 1361 |
|---|---|---|---|---|---|---|---|---|---|---|---|---|---|---|---|---|
| Leu | Ser | Ile | Pro | Leu | Phe | Leu | Ser | Tyr | His | Leu | Thr | Asn | Glu | Pro | Phe | |
| 165 | | | | | 170 | | | | | 175 | | | | | 180 | |

| CAT | AAT | CTC | TCT | CTC | CCT | ACT | GAC | ATC | TAC | ACC | CAC | CAG | GTA | GCT | TGT | 1409 |
|---|---|---|---|---|---|---|---|---|---|---|---|---|---|---|---|---|
| His | Asn | Leu | Ser | Leu | Pro | Thr | Asp | Ile | Tyr | Thr | His | Gln | Val | Ala | Cys | |
| | | | | 185 | | | | | 190 | | | | | 195 | | |

| GTG | GAG | ATT | TGG | CCT | TCT | AAA | CTG | AAC | CAA | CTC | CTC | TTT | TCT | ACA | TCA | 1457 |
|---|---|---|---|---|---|---|---|---|---|---|---|---|---|---|---|---|
| Val | Glu | Ile | Trp | Pro | Ser | Lys | Leu | Asn | Gln | Leu | Leu | Phe | Ser | Thr | Ser | |
| | | | 200 | | | | | 205 | | | | | 210 | | | |

| TTA | TTT | ATG | CTC | CAG | TAT | TTT | GTC | CCT | CTG | GGT | TTC | ATT | CTT | ATC | TGC | 1505 |
|---|---|---|---|---|---|---|---|---|---|---|---|---|---|---|---|---|
| Leu | Phe | Met | Leu | Gln | Tyr | Phe | Val | Pro | Leu | Gly | Phe | Ile | Leu | Ile | Cys | |
| | | 215 | | | | | 220 | | | | | 225 | | | | |

| TAC | CTG | AAG | ATC | GTT | CTC | TGC | CTC | CGA | AAA | AGA | ACT | AGG | CAG | GTG | GAC | 1553 |
|---|---|---|---|---|---|---|---|---|---|---|---|---|---|---|---|---|
| Tyr | Leu | Lys | Ile | Val | Leu | Cys | Leu | Arg | Lys | Arg | Thr | Arg | Gln | Val | Asp | |
| 230 | | | | | 235 | | | | | 240 | | | | | | |

| AGG | AGA | AAG | GAA | AAT | AAG | AGC | CGT | CTC | AAT | GAG | AAC | AAG | AGG | GTA | AAT | 1601 |
|---|---|---|---|---|---|---|---|---|---|---|---|---|---|---|---|---|
| Arg | Arg | Lys | Glu | Asn | Lys | Ser | Arg | Leu | Asn | Glu | Asn | Lys | Arg | Val | Asn | |
| 245 | | | | 250 | | | | | 255 | | | | | 260 | | |

| GTG | ATG | TTG | ATT | TCC | ATC | GTA | GTG | ACT | TTT | GGA | GCC | TGC | TGG | TTG | CCC | 1649 |
|---|---|---|---|---|---|---|---|---|---|---|---|---|---|---|---|---|
| Val | Met | Leu | Ile | Ser | Ile | Val | Val | Thr | Phe | Gly | Ala | Cys | Trp | Leu | Pro | |
| | | | | 265 | | | | | 270 | | | | | 275 | | |

| TTG | AAC | ATT | TTC | AAT | GTC | ATC | TTC | GAC | TGG | TAT | CAT | GAG | ATG | CTG | ATG | 1697 |
|---|---|---|---|---|---|---|---|---|---|---|---|---|---|---|---|---|

| | | | | | | | | | | | | | | | | |
|---|---|---|---|---|---|---|---|---|---|---|---|---|---|---|---|---|
|Leu|Asn|Ile|Phe|Asn|Val|Ile|Phe|Asp|Trp|Tyr|His|Glu|Met|Leu|Met| |
| | | |280| | | |285| | | |290| | | | | |

| | | | | | | | | | | | | | | | | |
|---|---|---|---|---|---|---|---|---|---|---|---|---|---|---|---|---|
|AGC|TGC|CAC|CAC|GAC|CTG|GTA|TTT|GTA|GTT|TGC|CAC|TTG|ATT|GCT|ATG|1745|
|Ser|Cys|His|His|Asp|Leu|Val|Phe|Val|Val|Cys|His|Leu|Ile|Ala|Met| |
| | |295| | | | |300| | | | |305| | | | |
|GTT|TCT|ACT|TGC|ATA|AAT|CCT|CTC|TTT|TAT|GGA|TTT|CTC|AAC|AAA|AAC|1793|
|Val|Ser|Thr|Cys|Ile|Asn|Pro|Leu|Phe|Tyr|Gly|Phe|Leu|Asn|Lys|Asn| |
| | |310| | | |315| | | | |320| | | | | |
|TTC|CAG|AAG|GAT|CTA|ATG|ATG|CTT|ATT|CAC|CAC|TGT|TGG|TGT|GGT|GAA|1841|
|Phe|Gln|Lys|Asp|Leu|Met|Met|Leu|Ile|His|His|Cys|Trp|Cys|Gly|Glu| |
|325| | | | |330| | | |335| | | | | |340| |
|CCT|CAG|GAA|AGT|TAT|GAA|AAT|ATT|GCC|ATG|TCT|ACT|ATG|CAC|ACA|GAT|1889|
|Pro|Gln|Glu|Ser|Tyr|Glu|Asn|Ile|Ala|Met|Ser|Thr|Met|His|Thr|Asp| |
| | | | |345| | | |350| | | | |355| | | |
|GAA|TCC|AAG|GGA|TCA|TTA|AAA|CTG|GCT|CAC|ATA|CCA|ACA|GGC|ATA|TAG|1937|
|Glu|Ser|Lys|Gly|Ser|Leu|Lys|Leu|Ala|His|Ile|Pro|Thr|Gly|Ile|*| |
| | | |360| | | |365| | | | |370| | | | |

| | | | | | |
|---|---|---|---|---|---|---|
|AAACTGGTAA|GCAAATCAA|AGCCCTTCTG|TTATGAAAGA|AAGAGAAGAA|ATAGTATGGA|1997|
|ATAGGGCAAG|GTGCAGAGGA|AGCCAGACTT|AAACACATAA|TATCTTTGGG|CCCAGTTTTG|2057|
|CTTTAAGTTA|AGCATGTCTA|CTCCATTCAG|CCATAGAACA|CACAGAGATT|TATCCCTACC|2117|
|CTTTCTTTTT|TTCCTTTGGA|AGAATAATAA|CTTAAACAAC|CTAGACATCA|TTACTGAGGA|2177|
|AGAGAACAAA|AATGAGAGAG|CATACAAGGA|CAGCAGAGAT|GTCTGGGGTA|CAAAATTCAC|2237|
|GTTATTCGCT|GGAATAGCTA|GAAAGTTATT|AGTTGTGCTG|CAG| |2280|

( 2 ) INFORMATION FOR SEQ ID NO:6:

( i ) SEQUENCE CHARACTERISTICS:
        ( A ) LENGTH: 371 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
|Met|Glu|Val|Leu|Thr|Asn|Gln|Pro|Thr|Pro|Asn|Lys|Thr|Ser|Gly|Lys|
|1| | | |5| | | |10| | | |15| | |
|Ser|Asn|Asn|Ser|Ala|Phe|Phe|Tyr|Phe|Glu|Ser|Cys|Gln|Pro|Pro|Phe|
| | | |20| | | |25| | | |30| | | | |
|Leu|Ala|Ile|Leu|Leu|Leu|Leu|Ile|Ala|Tyr|Thr|Val|Ile|Leu|Ile|Met|
| | |35| | | |40| | | |45| | | | | |
|Gly|Ile|Phe|Gly|Asn|Leu|Ser|Leu|Ile|Ile|Ile|Phe|Lys|Lys|Gln| |
| |50| | | |55| | | |60| | | | | | |
|Arg|Glu|Ala|Gln|Asn|Val|Thr|Asn|Ile|Leu|Ile|Ala|Asn|Leu|Ser|Leu|
|65| | | |70| | | |75| | | |80| | | |
|Ser|Asp|Ile|Leu|Val|Cys|Val|Met|Cys|Ile|Pro|Phe|Thr|Val|Ile|Tyr|
| | | |85| | | |90| | | |95| | | | |
|Thr|Leu|Met|Asp|His|Trp|Val|Phe|Gly|Asn|Thr|Met|Cys|Lys|Leu|Thr|
| | |100| | | |105| | | |110| | | | | |
|Ser|Tyr|Val|Gln|Ser|Val|Ser|Val|Ser|Val|Ser|Ile|Phe|Ser|Leu|Val|
| | |115| | | |120| | | |125| | | | | |
|Leu|Ile|Ala|Ile|Glu|Arg|Tyr|Gln|Leu|Ile|Val|Asn|Pro|Arg|Gly|Trp|
| |130| | | |135| | | |140| | | | | | |
|Lys|Pro|Arg|Val|Ala|His|Ala|Tyr|Trp|Gly|Ile|Ile|Leu|Ile|Trp|Leu|
|145| | | |150| | | |155| | | |160| | | |
|Ile|Ser|Leu|Thr|Leu|Ser|Ile|Pro|Leu|Phe|Leu|Ser|Tyr|His|Leu|Thr|
| | | |165| | | |170| | | |175| | | | |

```
Asn  Glu  Pro  Phe  His  Asn  Leu  Ser  Leu  Pro  Thr  Asp  Ile  Tyr  Thr  His
               180                      185                     190

Gln  Val  Ala  Cys  Val  Glu  Ile  Trp  Pro  Ser  Lys  Leu  Asn  Gln  Leu  Leu
          195                     200                    205

Phe  Ser  Thr  Ser  Leu  Phe  Met  Leu  Gln  Tyr  Phe  Val  Pro  Leu  Gly  Phe
     210                     215                     220

Ile  Leu  Ile  Cys  Tyr  Leu  Lys  Ile  Val  Leu  Cys  Leu  Arg  Lys  Arg  Thr
225                      230                    235                         240

Arg  Gln  Val  Asp  Arg  Arg  Lys  Glu  Asn  Lys  Ser  Arg  Leu  Asn  Glu  Asn
               245                     250                          255

Lys  Arg  Val  Asn  Val  Met  Leu  Ile  Ser  Ile  Val  Val  Thr  Phe  Gly  Ala
               260                     265                     270

Cys  Trp  Leu  Pro  Leu  Asn  Ile  Phe  Asn  Val  Ile  Phe  Asp  Trp  Tyr  His
          275                     280                     285

Glu  Met  Leu  Met  Ser  Cys  His  His  Asp  Leu  Val  Phe  Val  Val  Cys  His
     290                     295                     300

Leu  Ile  Ala  Met  Val  Ser  Thr  Cys  Ile  Asn  Pro  Leu  Phe  Tyr  Gly  Phe
305                      310                    315                         320

Leu  Asn  Lys  Asn  Phe  Gln  Lys  Asp  Leu  Met  Met  Leu  Ile  His  His  Cys
               325                     330                          335

Trp  Cys  Gly  Glu  Pro  Gln  Glu  Ser  Tyr  Glu  Asn  Ile  Ala  Met  Ser  Thr
               340                     345                     350

Met  His  Thr  Asp  Glu  Ser  Lys  Gly  Ser  Leu  Lys  Leu  Ala  His  Ile  Pro
          355                     360                    365

Thr  Gly  Ile
     370
```

( 2 ) INFORMATION FOR SEQ ID NO:7:

( i ) SEQUENCE CHARACTERISTICS:
        ( A ) LENGTH: 382 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:7:

```
Met  Asn  Ser  Thr  Leu  Phe  Ser  Lys  Val  Glu  Asn  His  Ser  Ile  His  Tyr
1                   5                   10                          15

Asn  Ala  Ser  Glu  Asn  Ser  Pro  Leu  Leu  Ala  Phe  Glu  Asn  Asp  Asp  Cys
               20                      25                     30

His  Leu  Pro  Leu  Ala  Val  Ile  Phe  Thr  Leu  Ala  Leu  Ala  Tyr  Gly  Ala
          35                      40                     45

Val  Ile  Ile  Leu  Gly  Val  Ser  Gly  Asn  Leu  Ala  Leu  Ile  Ile  Ile  Ile
     50                      55                     60

Leu  Lys  Gln  Lys  Glu  Met  Arg  Asn  Val  Thr  Asn  Ile  Leu  Ile  Val  Asn
65                       70                     75                          80

Leu  Ser  Phe  Ser  Asp  Leu  Leu  Val  Ala  Val  Met  Cys  Leu  Pro  Phe  Thr
               85                      90                          95

Phe  Val  Tyr  Thr  Leu  Met  Asp  His  Trp  Val  Phe  Gly  Glu  Thr  Met  Cys
               100                     105                    110

Lys  Leu  Asn  Pro  Phe  Val  Gln  Cys  Val  Ser  Ile  Thr  Val  Ser  Ile  Phe
          115                     120                    125
```

| | | | | | | | | | | | | |
|---|---|---|---|---|---|---|---|---|---|---|---|---|
| Ser | Leu | Val | Leu | Ile | Ala | Val | Glu | Arg | His | Gln | Leu | Ile | Ile | Asn | Pro |
| | 130 | | | | 135 | | | | | 140 | | | | | |
| Arg | Gly | Trp | Arg | Pro | Asn | Asn | Arg | His | Ala | Tyr | Ile | Gly | Ile | Thr | Val |
| 145 | | | | | 150 | | | | | 155 | | | | | 160 |
| Ile | Trp | Val | Leu | Ala | Val | Ala | Ser | Ser | Leu | Pro | Phe | Val | Ile | Tyr | Gln |
| | | | | 165 | | | | | 170 | | | | | 175 | |
| Ile | Leu | Thr | Asp | Glu | Pro | Phe | Gln | Asn | Val | Ser | Leu | Ala | Ala | Phe | Lys |
| | | | 180 | | | | | 185 | | | | | 190 | | |
| Asp | Lys | Tyr | Val | Cys | Phe | Asp | Lys | Phe | Pro | Ser | Asp | Ser | His | Arg | Leu |
| | | 195 | | | | | 200 | | | | | 205 | | | |
| Ser | Tyr | Thr | Thr | Leu | Leu | Leu | Val | Leu | Gln | Tyr | Phe | Gly | Pro | Leu | Cys |
| | | 210 | | | | 215 | | | | | 220 | | | | |
| Phe | Ile | Phe | Ile | Cys | Tyr | Phe | Lys | Ile | Tyr | Ile | Arg | Leu | Lys | Arg | Arg |
| 225 | | | | | 230 | | | | | 235 | | | | | 240 |
| Asn | Asn | Met | Met | Asp | Lys | Ile | Arg | Asp | Ser | Lys | Tyr | Arg | Ser | Ser | Glu |
| | | | | 245 | | | | | 250 | | | | | 255 | |
| Thr | Lys | Arg | Ile | Asn | Ile | Met | Leu | Leu | Ser | Ile | Val | Val | Ala | Phe | Ala |
| | | | 260 | | | | | 265 | | | | | 270 | | |
| Val | Cys | Trp | Leu | Pro | Leu | Thr | Ile | Phe | Asn | Thr | Val | Phe | Asp | Trp | Asn |
| | | 275 | | | | | 280 | | | | | 285 | | | |
| His | Gln | Ile | Ile | Ala | Thr | Cys | Asn | His | Asn | Leu | Leu | Phe | Leu | Leu | Cys |
| | 290 | | | | | 295 | | | | | 300 | | | | |
| His | Leu | Thr | Ala | Met | Ile | Ser | Thr | Cys | Val | Asn | Pro | Ile | Phe | Tyr | Gly |
| 305 | | | | | 310 | | | | | 315 | | | | | 320 |
| Phe | Leu | Asn | Lys | Asn | Phe | Gln | Arg | Asp | Leu | Gln | Phe | Phe | Phe | Asn | Phe |
| | | | | 325 | | | | | 330 | | | | | 335 | |
| Cys | Asp | Phe | Arg | Ser | Arg | Asp | Asp | Tyr | Glu | Thr | Ile | Ala | Met | Ser |
| | | | 340 | | | | | 345 | | | | | 350 | | |
| Thr | Met | His | Thr | Asp | Val | Ser | Lys | Thr | Ser | Leu | Lys | Gln | Ala | Ser | Pro |
| | | 355 | | | | | 360 | | | | | 365 | | | |
| Val | Ala | Phe | Lys | Lys | Ile | Ser | Met | Asn | Asp | Asn | Glu | Lys | Val |
| | 370 | | | | | 375 | | | | | 380 | | | | |

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:8:

ACCAGTGGCA AGAGCAACAA C                                  21

( 2 ) INFORMATION FOR SEQ ID NO:9:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:9:

CTCATTGGTG AGGTGGTAGG AC                                                                           22

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:10:

GGGCATTTTT GGAAACCTCT C                                                                            21

(2) INFORMATION FOR SEQ ID NO:11:

(i) SEQUENCE CHARACTERISTICS:
        (A) LENGTH: 1499 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:11:

| | | | | | | |
|---|---|---|---|---|---|---|
| CCCCGGGCTG | CAGGAATTCC | CACATGTTTC | CATCAAATAC | AGACACAGAT | CAGGGAAGAT | 60 |
| TAAACCCTAC | TAATTTCTCG | TCGGATGCCT | CACAACAAGG | TGCCTTCCAA | GAACTAATGG | 120 |
| CCAAAATATC | CACCCACAAC | ACAAATAAGC | TTAGAAAATC | TCTTCTTACA | ATCCTGACAC | 180 |
| AATGGAAGTT | TCCCTAAACC | ACCCAGCATC | TAATACAACC | AGCACAAAGA | ACAACAACTC | 240 |
| GGCATTTTTT | TACTTTGAGT | CCTGTCAACC | CCCTTCTCCA | GCTTACTCC | TATTATGCAT | 300 |
| AGCCTATACT | GTGGTCTTAA | TTGTGGGCCT | TTTTGGAAAC | CTCTCTCTCA | TCATCATCAT | 360 |
| CTTTAAGAAG | CAGAGAAAAG | CTCAGAATTT | CACCAGCATA | CTGATTGCCA | ATCTCTCCCT | 420 |
| CTCTGATACC | TTGGTGTGTG | TCATGTGCAT | CCATTTTACT | ATCATCTACA | CTCTGATGGA | 480 |
| CCACTGGATA | TTTGGGGATA | CCATGTGCAG | ACTCACATCC | TATGTGCAGA | GTGTCTCAAT | 540 |
| CTCTGTGTCC | ATATTCTCAC | TTGTATTCAC | TGCTGTCGAA | AGATATCAGC | TAATTGTGAA | 600 |
| CCCCCGTGGC | TGGAAGCCCA | GTGTGACTCA | TGCCTACTGG | GGCATCACAC | TGATTTGGCT | 660 |
| GTTTTCCCTT | CTGCTGTCTA | TTCCCTTCTT | CCTGTCCTAC | CACCTCACTG | ATGAGCCCTT | 720 |
| CCACAACCTC | TCTCTCCCCA | CTGACCTCTA | CACCCACCAG | GTGGCCTGTG | TGGAGAACTG | 780 |
| GCCCTCCAAA | AAGGACCGGC | TGCTCTTCAC | CACCTCCCTT | TTTCTGCTGC | AGTATTTGT | 840 |
| TCCTCTAGGC | TTCATCCTCA | TCTGCTACTT | GAAGATTGTT | ATCTGCCTCC | GCAGGAGAAA | 900 |
| TGCAAAGGTA | GATAAGAAGA | AGGAAAATGA | GGGCCGGCTC | AATGAGAACA | AGAGGATCAA | 960 |
| CACAATGTTG | ATTTCCATCG | TGGTGACCTT | TGGAGCCTGC | TGGCTGCCCC | CGAATATCTT | 1020 |
| CAATGTCATC | TTTGACTGGT | ATCATGAGGT | GCTGATGAGC | TGCCACCACG | ACCTGGTATT | 1080 |
| TGTAGTTTGC | CACTTGGTTG | CTATGGTTTC | CACATGTATA | AACCCTCTCT | TTTATGGCTT | 1140 |
| TCTCAACAAA | AATTTCCAAA | AGGACCTGGT | AGTGCTTATT | CACCACTGCT | GGTGCTTCAC | 1200 |
| ACCTCAGGAA | AGATGTGAAA | ATATTGCCAT | CTCCACTATG | CACACAGACT | CCAAGAGGTC | 1260 |
| TTTAAGATTG | GCTCGTATAA | CAACAGGTAT | ATGAAAATTG | ATAATGCTGA | AGCTCTTCTT | 1320 |

| GAATGGGAGC | TGGACAGGTA | ATGGTGGGAA | TAGGGCAAGA | TGCAGAAAGA | AGAAACCAGA | 1380 |
| ACCAAAAATA | GCAACTTTAT | ACCCACTTTT | CCTTTAGGCT | AAGACTGCCT | GTCTCATATG | 1440 |
| TCTATCCAAC | ACACCCTCCG | GAATTCGATA | TCAAGCTTAT | CGATACCGTC | GACCTCGAG | 1499 |

( 2 ) INFORMATION FOR SEQ ID NO:12:

( i ) SEQUENCE CHARACTERISTICS:
        ( A ) LENGTH: 370 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

```
Met Glu Val Ser Leu Asn His Pro Ala Ser Asn Thr Thr Ser Thr Lys
  1               5                  10                  15

Asn Asn Asn Ser Ala Phe Phe Tyr Phe Glu Ser Cys Gln Pro Pro Ser
             20                  25                  30

Pro Ala Leu Leu Leu Leu Cys Ile Ala Tyr Thr Val Val Leu Ile Val
         35                  40                  45

Gly Leu Phe Gly Asn Leu Ser Leu Ile Ile Ile Phe Lys Lys Gln
 50                      55                  60

Arg Lys Ala Gln Asn Phe Thr Ser Ile Leu Ile Ala Asn Leu Ser Leu
 65                  70                  75                  80

Ser Asp Thr Leu Val Cys Val Met Cys Ile His Phe Thr Ile Ile Tyr
                     85                  90                  95

Thr Leu Met Asp His Trp Ile Phe Gly Asp Thr Met Cys Arg Leu Thr
             100                 105                 110

Ser Tyr Val Gln Ser Val Ser Ile Ser Val Ser Ile Phe Ser Leu Val
         115                 120                 125

Phe Thr Ala Val Glu Arg Tyr Gln Leu Ile Val Asn Pro Arg Gly Trp
 130                 135                 140

Lys Pro Ser Val Thr His Ala Tyr Trp Gly Ile Thr Leu Ile Trp Leu
145                 150                 155                 160

Phe Ser Leu Leu Leu Ser Ile Pro Phe Phe Leu Ser Tyr His Leu Thr
                 165                 170                 175

Asp Glu Pro Phe His Asn Leu Ser Leu Pro Thr Asp Leu Tyr Thr His
             180                 185                 190

Gln Val Ala Cys Val Glu Asn Trp Pro Ser Lys Lys Asp Arg Leu Leu
         195                 200                 205

Phe Thr Thr Ser Leu Phe Leu Leu Gln Tyr Phe Val Pro Leu Gly Phe
 210                 215                 220

Ile Leu Ile Cys Tyr Leu Lys Ile Val Ile Cys Leu Arg Arg Arg Asn
225                 230                 235                 240

Ala Lys Val Asp Lys Lys Glu Asn Glu Gly Arg Leu Asn Glu Asn
                 245                 250                 255

Lys Arg Ile Asn Thr Met Leu Ile Ser Ile Val Val Thr Phe Gly Ala
         260                 265                 270

Cys Trp Leu Pro Pro Asn Ile Phe Asn Val Ile Phe Asp Trp Tyr His
             275                 280                 285

Glu Val Leu Met Ser Cys His His Asp Leu Val Phe Val Val Cys His
         290                 295                 300

Leu Val Ala Met Val Ser Thr Cys Ile Asn Pro Leu Phe Tyr Gly Phe
305                 310                 315                 320

Leu Asn Lys Asn Phe Gln Lys Asp Leu Val Val Leu Ile His His Cys
```

|  | 325 |  |  |  |  |  | 330 |  |  |  |  | 335 |  |  |
|---|---|---|---|---|---|---|---|---|---|---|---|---|---|---|
| Trp | Cys | Phe | Thr 340 | Pro | Gln | Glu | Arg | Cys 345 | Glu | Asn | Ile | Ala | Ile 350 | Ser | Thr |
| Met | His | Thr 355 | Asp | Ser | Lys | Arg | Ser 360 | Leu | Arg | Leu | Ala | Arg 365 | Ile | Thr | Thr |
| Gly | Ile 370 |

What is claimed is:

1. A neuropeptide Y Yx receptor produced by culturing a cell transformed by an expression vector containing a DNA sequence selected from the group consisting of a sequence as shown in SEQ. I.D. NO. 5 and a fragment of the sequence shown in SEQ. I.D. NO. 5 comprising bases 822 to 1934 and optionally recovering the neuropeptide Y Yx receptor.

2. The neuropeptide Y Yx receptor of claim 1, which is characterized by a pharmacological binding profile with affinities of PYY≅NPY≅[Leu$^{31}$Pro$^{34}$]NPY≅NPY(2–36)>NPY(13–36).

3. A neuropeptide Y Yx receptor, in substantially pure form, which is characterized by a pharmacological binding profile with affinities of PYY≅NPY≅[Leu$^{31}$Pro$^{34}$]NPY≅NPY(2–36)>NPY(13–36).

4. A neuropeptide Y Yx receptor produced by culturing a cell transformed by an expression vector containing a DNA sequence selected from the group consisting of the sequence shown in SEQ. I.D. NO. 11 and a fragment of the sequence shown in SEQ. I.D. NO. 11 comprising bases 182 to 1291 and optionally recovering the neuropeptide Y Yx receptor.

5. The neuropeptide Y Yx receptor of claim 4, which is characterized by a pharmacological binding profile with affinities of PYY≅NPY≅[Leu$^{31}$Pro$^{34}$]NPY≅NPY(2–36)>NPY(13–36).

6. A neuropeptide Y Yx receptor in substantially pure form comprising an amino acid sequence selected from the group consisting of a sequence as shown in SEQ. I.D. NO. 6, and a sequence as shown in SEQ. I.D. NO. 12.

7. The neuropeptide Y Yx receptor of claim 6, wherein the receptor has an amino acid sequence as shown in SEQ. I.D. NO. 6.

8. The neuropeptide Y Yx receptor of claim 6, wherein the receptor has an amino acid sequence as shown in SEQ. I.D. NO. 12.

* * * * *